(12) United States Patent
Nash et al.

(10) Patent No.: US 7,666,161 B2
(45) Date of Patent: Feb. 23, 2010

(54) THROMBECTOMY AND SOFT DEBRIS REMOVAL DEVICE

(75) Inventors: John E. Nash, Chester Springs, PA (US); Greg Walters, Exton, PA (US); Dennis M. Sauro, Glenmoore, PA (US); Mark Eberhart, Glenmoore, PA (US); William T. Fisher, Schwenksville, PA (US); Douglas G. Evans, Downingtown, PA (US)

(73) Assignee: The Spectranetics Corporation, Colorado Springs, CO (US)

( * ) Notice: Subject to any disclaimer, the term of this patent is extended or adjusted under 35 U.S.C. 154(b) by 0 days.

(21) Appl. No.: 11/751,443

(22) Filed: May 21, 2007

(65) Prior Publication Data

US 2007/0282303 A1 Dec. 6, 2007

Related U.S. Application Data

(63) Continuation-in-part of application No. 10/832,830, filed on Apr. 27, 2004.

(51) Int. Cl.
*A61B 17/20* (2006.01)
*A61B 17/22* (2006.01)
*A61M 25/00* (2006.01)

(52) U.S. Cl. .................. 604/22; 606/159; 604/523

(58) Field of Classification Search ............ 604/32–35, 604/43, 118, 131, 152, 155, 22, 39, 154, 604/171; 606/159
See application file for complete search history.

(56) References Cited

U.S. PATENT DOCUMENTS 4,196,729 A * 4/1980 Nathan et al. ............... 604/66
4,445,509 A 5/1984 Auth
4,589,412 A 5/1986 Kensey (Continued)

FOREIGN PATENT DOCUMENTS

EP 0582533 A1 2/1994

(Continued)

OTHER PUBLICATIONS

Straub Rotarex® Animation, http://www.straubmedical.com/?lid=1 &mid=61, May 8, 2008.

(Continued)

*Primary Examiner*—Kevin C Sirmons
*Assistant Examiner*—Bradley J Osinski
(74) *Attorney, Agent, or Firm*—Townsend and Townsend and Crew LLP

(57) ABSTRACT

A device suitable for removing material from a living being is provided, featuring an infusate pump, and an aspiration pump, both powered by a motor. The aspiration pump and infusate pump preferably feature a helical pumping mechanism, and operate at a high rate of rotation, thereby ensuring adequate pumping performance and flexibility. Additionally, a narrow crossing profile is maintained, ensuring that the device may reach more tortuous regions of the vasculature. In one embodiment, the system comprises a wire-guided monorail catheter with a working head mounted on a flexible portion of the catheter that can laterally displace away from the guide wire to facilitate thrombus removal. The working head may be operated to separate and move away from the guide wire to come within a closer proximity of the obstructive material to more effectively remove it from the vessel.

25 Claims, 9 Drawing Sheets

U.S. PATENT DOCUMENTS

| | | | |
|---|---|---|---|
| 4,631,052 | A | 12/1986 | Kensey |
| 4,686,982 | A | 8/1987 | Nash |
| 4,696,667 | A | 9/1987 | Masch |
| 4,700,705 | A | 10/1987 | Kensey et al. |
| 4,728,319 | A | 3/1988 | Masch |
| 4,747,821 | A | 5/1988 | Kensey et al. |
| 4,749,376 | A | 6/1988 | Kensey et al. |
| 4,781,186 | A | 11/1988 | Simpson et al. |
| 4,790,812 | A | 12/1988 | Hawkins, Jr. et al. |
| 4,790,813 | A | 12/1988 | Kensey |
| 4,857,045 | A | 8/1989 | Rydell |
| 4,857,046 | A | 8/1989 | Stevens et al. |
| 4,979,939 | A | 12/1990 | Shiber |
| 5,000,185 | A | 3/1991 | Yock |
| 5,074,841 | A | 12/1991 | Ademovic et al. |
| 5,078,722 | A | 1/1992 | Stevens |
| 5,084,052 | A | 1/1992 | Jacobs |
| 5,135,483 | A | 8/1992 | Wagner et al. |
| 5,195,954 | A | 3/1993 | Pesch-Schnepp et al. |
| 5,226,909 | A | 7/1993 | Evans et al. |
| 5,242,460 | A | 9/1993 | Klein et al. |
| 5,261,877 | A | 11/1993 | Fine et al. |
| 5,269,751 | A | 12/1993 | Kaliman et al. |
| 5,284,486 | A | 2/1994 | Kotula et al. |
| 5,312,427 | A | 5/1994 | Shturman |
| 5,334,211 | A | 8/1994 | Shiber |
| 5,358,509 | A | 10/1994 | Fine et al. |
| 5,360,432 | A | 11/1994 | Shturman |
| 5,370,651 | A | 12/1994 | Summers |
| 5,395,311 | A | 3/1995 | Andrews |
| 5,417,703 | A | 5/1995 | Brown et al. |
| 5,549,546 | A * | 8/1996 | Schneider et al. ............. 604/26 |
| 5,569,275 | A | 10/1996 | Kotula et al. |
| 5,653,696 | A | 8/1997 | Shiber |
| 5,695,507 | A | 12/1997 | Auth et al. |
| 5,728,129 | A | 3/1998 | Summers |
| 5,743,891 | A | 4/1998 | Tolkoff et al. |
| 5,746,758 | A | 5/1998 | Nordgren et al. |
| 5,749,357 | A * | 5/1998 | Linder ................... 128/200.26 |
| 5,779,721 | A | 7/1998 | Nash |
| 5,853,384 | A | 12/1998 | Bair |
| 5,873,882 | A | 2/1999 | Straub et al. |
| 5,876,414 | A | 3/1999 | Straub |
| 5,879,361 | A | 3/1999 | Nash |
| 5,897,534 | A | 4/1999 | Heim et al. |
| 5,997,558 | A | 12/1999 | Nash |
| 6,001,112 | A | 12/1999 | Taylor |
| 6,080,170 | A | 6/2000 | Nash et al. |
| 6,117,149 | A | 9/2000 | Sorensen et al. |
| 6,156,046 | A | 12/2000 | Passafaro et al. |
| 6,186,975 | B1 | 2/2001 | Sakai |
| 6,206,898 | B1 | 3/2001 | Honeycutt et al. |
| 6,206,900 | B1 | 3/2001 | Tabatabaei et al. |
| 6,238,405 | B1 | 5/2001 | Findlay, III et al. |
| 6,451,036 | B1 | 9/2002 | Heitzmann et al. |
| 6,454,775 | B1 | 9/2002 | Demarais |
| 6,454,779 | B1 | 9/2002 | Taylor |
| 6,482,217 | B1 | 11/2002 | Pintor et al. |
| 6,494,890 | B1 * | 12/2002 | Shturman et al. ........... 606/159 |
| 6,524,323 | B1 | 2/2003 | Nash et al. |
| 6,554,799 | B1 | 4/2003 | Hatamura et al. |
| 6,569,147 | B1 | 5/2003 | Evans et al. |
| 6,592,335 | B2 | 7/2003 | Rosefsky |
| 6,635,070 | B2 | 10/2003 | Leeflang et al. |
| 6,638,233 | B2 | 10/2003 | Corvi et al. |
| 6,660,014 | B2 | 12/2003 | Demarais et al. |
| 6,666,874 | B2 | 12/2003 | Heitzmann et al. |
| 6,669,662 | B1 | 12/2003 | Webler |
| 6,682,543 | B2 | 1/2004 | Barbut et al. |
| 6,692,460 | B1 | 2/2004 | Jayaraman |
| 6,702,830 | B1 * | 3/2004 | Demarais et al. ............ 606/159 |
| 6,818,001 | B2 | 11/2004 | Wulfman et al. |
| 6,843,797 | B2 | 1/2005 | Nash et al. |
| 6,929,633 | B2 | 8/2005 | Evans et al. |
| 6,945,977 | B2 | 9/2005 | Demarais et al. |
| 7,172,610 | B2 | 2/2007 | Heitzmann et al. |
| 2001/0031981 | A1 | 10/2001 | Evans et al. |
| 2002/0173819 | A1 | 11/2002 | Leeflang et al. |
| 2002/0188276 | A1 | 12/2002 | Evans et al. |
| 2002/0188307 | A1 | 12/2002 | Pintor et al. |
| 2003/0055444 | A1 | 3/2003 | Evans et al. |
| 2003/0055445 | A1 | 3/2003 | Evans et al. |
| 2003/0139751 | A1 | 7/2003 | Evans et al. |
| 2003/0144875 | A1 | 7/2003 | Suffin et al. |
| 2007/0197959 | A1 | 8/2007 | Panotopoulos |
| 2007/0282303 | A1 | 12/2007 | Nash et al. |
| 2008/0097499 | A1 | 4/2008 | Nash et al. |

FOREIGN PATENT DOCUMENTS

| | | |
|---|---|---|
| EP | 1870044 A1 | 12/2007 |
| WO | WO94/24941 | 11/1994 |
| WO | WO96/29941 | 10/1996 |
| WO | WO00/54659 | 9/2000 |
| WO | WO01/19444 | 3/2001 |

OTHER PUBLICATIONS

Straub Rotarex ® System, http://www.straubmedical.com/?lid=1&mid=61, May 8, 2008.

EV3 Products—HELIX™ The Clot Buster® , Mechanical Thrombectomy Device, http://www.ev3.net/index.asp?page ID=76&marketSegmentID=3&productCategoryID=6&p, May 8, 2008.

EV3 Products, X-Size® , Thrombectomy Mechanical System, http://www.ev3.net/index.asp?page ID=76&marketSegmentID=ID=3&productCategoryID=6&p, May 8, 2008.

* cited by examiner

THROMBECTOMY AND SOFT DEBRIS REMOVAL DEVICE

CROSS-REFERENCE TO RELATED APPLICATIONS

This patent document is a Continuation-in-Part of copending and commonly owned U.S. patent application Ser. No. 10/832,830, filed Apr. 27, 2004 in the names of John E. Nash et al. and entitled, "Thrombectomy and Soft Debris Removal Device." The entire contents of this prior application are expressly incorporated by reference.

BACKGROUND OF THE INVENTION

This application relates generally to medical instruments and methods of use to remove occlusive material from a vessel, duct or lumen within the body of a living being, specifically relating to the removal of thrombus or soft tissue clots from vascular or other lumens. A preferred embodiment more particularly concerns a device useful for clearing lumens relying on a device, incorporating at least one pumping means, to aspirate the debris, thereby clearing a partial or complete blockage of the vessel or lumen.

Vascular disease affects a large population each year. Indications of vascular disease include blood clots in the vascular system, possibly resulting in deep venous thrombosis (DVT), embolisms or ischemia. The clots are formed by aggregations of thrombus and fibrin, resulting in partial or total occlusion of the vessel. Various approaches to treatment may be performed, including treatment with lysing agents to chemically disperse the occlusion, or mechanical restoration of patency to the vessel may be attempted, such as Catheter Directed Thrombolytic Therapy.

Mechanical thrombectomy devices may be used to restore patency to a vessel that had been at least partially occluded by material. For example, rotary catheters may employ a rotary cutting head, a rotating macerator or some homogenization device to remove the clot by the effects of a hydrodynamic vortex generated near the clot. Alternatively, some instruments repeatedly drum into the occlusive material, displacing and distorting the material in order to create a lumen therethrough, while leaving the material within the vessel. Arguably, for the long term benefit of the patient, it is desirable to effectuate the removal of the occlusive material, yet care must be taken to ensure that loose debris, such as fragments of thrombus, are unable to travel away from the site to cause a life threatening injury such as an embolism, stroke or heart attack.

Helical pump designs have been incorporated into medical devices, for example, Hatamura et al. in U.S. Pat. No. 6,554, 799 describes utilizing high-speed rotation of a fixed twin filament rotor for transferring liquids in an inflexible needle. Any leakage of fluid through the clearance between the rotors and the surrounding needle is minimized by the viscosity of the liquid in combination with high-speed rotation of the rotor.

Catheter instruments have been suggested or disclosed in the patent literature for effecting non-invasive or minimally invasive revascularization of occluded arteries. For example, in U.S. Pat. No. 4,445,509 granted to Auth, there is disclosed a recanalization catheter designed specifically for cutting away hard, abnormal deposits, such as atherosclerotic plaque, from the inside of an artery, while supposedly preserving the soft arterial tissue. That recanalizing catheter includes a sharp-edged, multi-fluted, rotating cutting tip mounted at the distal end of the catheter and arranged to be rotated by a flexible drive shaft extending down the center of the catheter. The rotation of the cutting head is stated as producing a "differential cutting" effect, whereupon the rotating blade creates a cutting action that removes the relatively hard deposits and selectively leaves the relatively soft tissue. Suction ports are provided to pull the hard particles produced by the cutting action into the catheter for removal at the proximal end thereof so that such particles do not flow distally of the catheter where they could have an adverse effect on the patients' body, as previously discussed.

Additional rotating burr designs have been described, for example, for use in clearing asymmetrical plaque build-up within a vessel. Shturman in U.S. Pat. No. 5,312,427 provides lateral directional control to an atherectomy device by deploying an exposed rotating burr, in such a way that it can be extended laterally away from a guidewire in a single axis and directed by a positioning wire having a pre-determined shape. In this manner, the rotating burr can be directed into the asymmetrical plaque lesion, and thereby prevent normal vascular tissue (not covered with plaque) from damage due to contact with the high-speed rotation of the exposed burr. Shturman et al. in U.S. Pat. No. 6,494,890, also describe a rotational atherectomy device having a rotating driveshaft with an eccentric enlarged diameter section having an abrasive surface for removing tissue. By the nature of the eccentric rotation, a larger diameter than the outer diameter of the enlarged section may be cleared from stenotic tissue.

Also granted to Auth, U.S. Pat. No. 5,695,507, describes a helically wound coil wire, entrained within a catheter, that may be used to clear a thrombus blocked-vessel by causing the insoluble fibrous meshed strands of fibrin to wrap themselves around the helical wire. As the drive cable and associated helical wire rotate, the fibrin of the thrombus material may be drawn to a port by suction applied at the proximal end, thereby engaging the fibrin with the rotating, wrapping action of the helical coil wire. Alternatively, without applying any vacuum, the fibrin may become wrapped around the wire by the friction between the wire and the thrombus or the "whirling" effect of the rapidly rotating wire. Furthermore, drug delivery may be accomplished through the same fluid path in the housing in which the coil wire is contained.

In U.S. Pat. No. 4,700,705, which is assigned to the same assignee as this invention and whose disclosure is incorporated by reference herein, there are disclosed and claimed catheters and methods of use for effecting the opening of a vessel, duct or lumen, such as the opening of a atherosclerotic restriction (partial or total occlusion) in an artery. These catheters are elongated flexible members of sufficient flexibility to enable them to be readily passed through the body of the patient to the situs of the atherosclerotic plaque in the artery to be opened. A working head is mounted at the distal end of the catheter and is arranged for high-speed rotation about the longitudinal axis of the catheter. In some embodiments the catheter may eject fluid at the working head to expedite the restriction-opening procedure.

In U.S. Pat. No. 4,747,821, which is also assigned to the same assignee as this invention and whose disclosure is incorporated by reference herein, there is disclosed and claimed other catheters particularly suited for revascularization of arteries. Each of those catheters includes a rotary working head having at least one non-sharp impacting surface to effect material removal without cutting. Moreover, those catheters are arranged to eject fluid adjacent the working head to expedite the revascularization procedure. In particular, the rotation of the working head produces a powerful, toroidal shaped vortex contiguous, or adjacent, with the working head, which has the effect of recirculating any particles that may have been broken off from the material forming the arterial restriction so that the working head repeatedly impacts those particles to reduce their size.

Other atherectomy devices for enlarging an opening in a blood vessel have been disclosed and claimed in the following U.S. Pat. Nos. 4,589,412; 4,631,052; 4,686,982; 4,749,376; 4,790,813; and 6,080,170 (which is assigned to the same assignee as this invention and whose disclosure is incorporated by reference herein).

In U.S. Pat. No. 5,074,841 granted to Ademovic et al., there is disclosed a catheter device for performing an atherectomy. The device features an exposed series of slots in an outer housing, with a helical cutting blade rotating therein. The helical cutting blade, in conjunction with the slots, serves to sever the material and the rotary motion draws the fragments towards a grinding face of a ferrule. The ground particulate material may then be directed into a pair of flushing lumens, and aided by saline delivered to the site through saline lumens, flushed away from the treatment site.

In U.S. Pat. No. 4,857,046 granted to Stevens et al., there is disclosed a catheter for removing deposits from the inner walls of a blood vessel to increase blood flow through the vessel. The '046 patent discloses a flexible catheter, having a center portion with helical pumping means within a catheter sheath, and having an enlarged distal tip for abrading the deposits off an inner wall of the vessel, the pumping means and abrading action of the distal tip driven by a proximal drive means.

In U.S. Pat. No. 5,078,722, granted to Stevens, there is disclosed a catheter for removing deposits from the inner wall of a vessel, without having an enlarged distal working head. The '722 patent features a rotatable and axially moveable cutting member at the distal end of the catheter which separates the deposits from the vessel wall by actuation of a circular cutting edge. The rotation of the cutting mechanism is driven by a tubular transmission, which has a helical wire spiraling about the exterior, forming a helical pumping mechanism within the catheter to remove the debris. As the debris accumulates within the catheter, the inner core member is removable to allow for cleaning, and subsequent replacement within the outer catheter. The axial movement and rotation of the cutting member is controlled by the attending physician manipulating an axially slidable and rotatable hardware at the proximal end of the tubular transmission to drive the cutting mechanism, alternatively, the rotary inner core may be energized by incorporation of an electric motor. The distal end of the catheter features an inflatable balloon, whose inflation causes the portion of the catheter opposite the balloon to be pushed into engagement with the inner wall lining of the vessel.

U.S. Pat. No. 5,876,414 granted to Straub, discloses a rotary catheter for clearing a vessel, incorporating a rotor, and optionally a stator, cutting mechanism to sever the material from the vessel wall. As the rotor rotates, dual cutting slots engage and sever the material. Furthermore, Straub discloses using a helical pumping mechanism to remove the debris generated by the cutting. The helical pumping mechanism being a helical coil wrapped around the torque transmitting wire, such that as the rotor is turned, the coiled wire serves as a screw pump to convey the debris proximally.

U.S. Pat. No. 4,728,319 granted to Masch discloses a catheter for cutting into a blockage in a vessel, the catheter having a spherical cutting head on the distal end to cut the blockage into fragments. The catheter further features a means to deliver an oxygenated infusate to the cutting mechanism in order to flush the debris away from the cutting mechanism and clear the cutting means. The catheter system features a drain passage through which vacuum is drawn, so that fragment-laden fluid is drained through the catheter. Masch further describes that in addition to, or in lieu of the vacuum application, a helical pumping mechanism may be used to convey the debris proximally, and away from the treatment site. In an embodiment employing a helical pump, the interactions between opposite handed spirals on the adjoining surfaces of the inner and outer tubes cause a pumping action.

U.S. Pat. No. 6,454,775 granted to Demarais et al., discloses a catheter for clearing a blocked vessel, having a rotatable wire macerator, such as an expandable wire basket, exposed at the distal end of the catheter to engage and fragment the thrombus within the blocked vessel as the rotation occurs. Preferably, the catheter device may incorporate a helical rotor in order to pump material proximally away from the macerator and the blockage site.

U.S. Pat. No. 6,702,830 is a continuation-in-part of Demarais et al.'s '775 patent, describing an over the wire material transport catheter capable of infusion and aspiration through the use of helical coiled wires rotating within a lumen to create an Archimedes screw pump. The screw pump impeller described by Demarais et al. features an inner tube or member, and a coiled wire rotor. In one embodiment, there is described a bi-directional catheter featuring a single lumen having a wire wrapped around the length of the lumen, coiled in one direction; and further having a second coiled wire inside the length of the lumen, coiled in the other direction. In this manner, rotation of the lumen will result in infusion and aspiration concurrently. In another embodiment, the catheter lumen may house separate, side-by-side lumens for an aspiration coiled pump and an infusion coiled pump. The pump impellers are inserted and run concurrently through the body and may terminate at spaced-apart ports along the catheter body in order to ensure the delivered agents receive adequate residence time within the blood vessel.

U.S. Pat. No. 6,238,405 granted to Findlay, discloses a catheter device for removing material having a rotatable screw thread distal end adjacent a shearing member also near the distal end, in order to fragment the clot material. The thrombus is drawn into the device in order to be macerated, by application of the "Archimedes" screw action at the distal end, in combination with applied vacuum at the proximal end of the device in fluid communication with the distal end. The shearing member serves to fragment the thrombus into a manageable particle size to prevent the device from clogging as the material is pulled the length of the catheter out of the body.

U.S. Pat. No. 5,261,877 granted to Fine et al., discloses a mechanical thrombectomy device having a high speed canalizing working head, which rotates to homogenize and facilitate removal of the thrombus, where the device is capable of delivering a fluid media into the lumen. The device features a helical coil wire serving as a bearing to enable the high-speed rotation of the distal tip, without the drive cable wearing through the guide catheter due to friction. The spiral drive cable is designed to be removed to facilitate introduction of infusate liquid through the now unobstructed central lumen.

U.S. Pat. No. 6,117,149 granted to Sorenson et al., discloses a device to remove ophthalmic lens material in a mammalian eye, having a working head at the distal end, driven by a drive shaft having a spiral bearing coil wire within a rigid sleeve. This device may preferably incorporate separate passageways for infusion of infusate liquid and aspiration of material. The patent describes the spiral gap between the individual convolutions of the helical wire serving as the infusate pathway, when pressure is applied to a supply reservoir.

U.S. Pat. No. 4,979,939 granted to Shiber, discloses an artherectomy system for removing an obstruction from a patient's vessel. Shiber describes a device having a rotatable coring catheter, which follows along and around a flexible guidewire. The rotatable coring catheter is constructed of coiled windings of shaped ribbon, such that in cross section ridges or steps are incorporated in by the windings, creating a spiral step or ridge. Furthermore the coring catheter features a sharpened edge at the end, in order to slice off material from the vessel wall. The guidewire is described as a single pilot wire having three helical coil wires wrapped around the length of the pilot wire. Furthermore, the pilot guidewire may be in the form of a hollow tube, in order to allow delivery of contrast medium or other fluid. In use, the rotation of the coring catheter causes the coring end to slice into the occlusive material, and the ridges or steps within the coring catheter, coupled with an aspirating force applied at the distal end of the catheter cause the material to be moved proximally away from the site within the body. The helical coil wires serve to counter the distal movement of the obstructing material while being cored, to restrain the cored material from freely rotating around the pilot wire, and to serve as a helical bearing. The helical wires surround the pilot wire are not driven by the rotation, only the outer catheter is rotatably driven. The material is drawn proximally into the rotating coring catheter, and is removed along with the catheter itself.

In U.S. Pat. No. 6,156,046, granted to Passafaro et al., there is disclosed a device for removal of occlusions in a lumen, having a removal means at the distal end of a torquing member, driven by a handheld controller. The device utilizes a specially shaped guidewire having a guide section serving to orient the cutting head in order to clear a sufficiently large passageway through the lumen. In one embodiment, the removal means features exposed cutting surfaces that rotate, causing the removal of material from the vessel wall. Passafaro describes that the torquing member is a triple coil wire, with the outermost coiled wire serving to move the debris proximally from the site, out of the body. Implementation of the Passafaro device requires the replacement of a standard guidewire with a guidewire incorporating a specially shaped guide section, in order to steer the exposed cutting surfaces to clear the lumen.

The prior art described does not disclose a device suitable for reaching narrow vasculature or lumens within the body in order to clear occlusive material, the device having shielded cutting elements to protect the vessel wall, the device serving to ensure partial to complete evacuation of the removed occlusive material by implementation of aspiration and infusate pumping means, capable of achieving and maintaining adequate aspiration vacuum levels and adequate infusate and aspiration flow rates, with the aspiration pumping forces generated by a screw pump contained within and running substantially the length of the inserted catheter body, capable of being used with a conventional guidewire.

It is the intent of this invention to overcome the shortcomings of the prior art in creating a flexible catheter system capable of providing adequate flow rates while extended into and conforming to the more tortuous regions of the vasculature of the living being.

SUMMARY OF THE INVENTION

It is an object of this invention to provide an efficient manner for the removal of obstructions in a vessel or lumen. This is achieved by providing an assembly for debris removal, incorporating an "Archimedes" screw pump to aspirate and clear debris from the body.

It is another object of the invention to provide a safe manner for the removal of obstructions in a vessel or lumen. This is achieved by providing a device wherein the cutting surfaces are shielded from direct contact with the lumen or vessel wall, and provisions are taken to prevent occlusive material from traveling further away from the site and into the body. Furthermore, provisions are made to minimize associated blood loss in the procedure, both in operation of the device as well as in the duration of time required for the performance of the procedure to restore patency to the vessel.

It is yet another object of the invention to provide a small diameter wire guided catheter, which can safely remove obstructions in a vessel or lumen which are located at a distance from the path of the guidewire. This is achieved, for example, by providing an embodiment of a catheter having a flexible portion containing a working head, which can laterally extend away from the guide wire such that the working head portion of the catheter can come within a closer proximity of the obstructive material to more effectively remove it from the vessel.

These and other objects of this invention may be achieved by providing a system for opening a lumen in an occluded or partially occluded vessel, e.g., a blood vessel of a living being's vascular system located downstream of another blood vessel, e.g., the aorta, from which blood will flow to the occluded blood vessel. In one embodiment, the system may feature a catheter assembly having an aspiration means, and an infusate delivery means. In a preferred version, the aspiration means is a version of a flexible screw conveyor.

In one embodiment, the system has a working head to facilitate thrombus removal. The working head may physically manipulate the thrombus (e.g., a macerating head, a cutting head, etc.) or the working head may affect the thrombus without making direct contact to the thrombus along the vessel wall (e.g., by creating currents to aid in aspiration, or deliver infusate jets, etc.) in order to remove the thrombus. In a preferred version, the working head is shielded within the catheter body, and only acts upon material that is pulled into openings strategically placed and sized in the catheter.

The device incorporating a helical screw pump that serves as a flexible screw conveyor is capable of navigating the more tortuous regions of the vascular system. The flexibility normally interferes with the operation of a screw pump; because as the catheter distorts in the flexed/stressed region, forming an oval shape in cross section, resulting in a larger clearance between the helix and the surrounding jacket. The present invention overcomes this drawback by rotating at a sufficiently high rate to overcome the pumping losses that occur in the flexed regions. Furthermore, pumping losses at the flexed region are minimized by the large number of windings for the helical pump system.

The cutting surfaces may be shielded, such that they are not able to come in contact with the vessel wall, but may serve to sever tissue and other material that is drawn into the device by the aspirating force created by the helical pump.

In yet another embodiment, the system comprises a wire-guided mono-rail catheter with a working head mounted on a flexible portion of the catheter that can laterally displace away from the guide wire to facilitate thrombus removal. The working head may be operated to separate and move away from the guide wire to come within a closer proximity of the obstructive material to more effectively remove it from the vessel. This embodiment allows relatively small diameter catheters of the subject invention to remove obstructive material from vessels that are much larger in diameter.

In yet another embodiment, the amount of lateral displacement of the working head from the guide wire can be controlled and adjusted by the operator to tune the activity of the device to effectively treat and remove debris within various sized vessels.

DETAILED DESCRIPTION OF PREFERRED EMBODIMENTS

The present invention provides an assembly having a sufficiently narrow crossing profile (for example, the cross-section of the inserted device at its widest point), and also having adequate flexibility such the invention is capable of operating while flexed and navigating into regions of a body of a living being in order to clear occlusive material, e.g. blood clots or plaque accumulation in a blood vessel or lumen.

The following description describes the catheter assembly, components and features depicted in the figures, wherein like numbers refer to like components.

In one embodiment, the catheter assembly features a pair of rotary helical pumps, the helical pumps serving the function of aspiration and infusate delivery, and may be operated independently by distinct sources of rotary power (e.g., electrical motors, air turbine, hydraulic, etc.). In an embodiment, the rotor for each of the helical pump mechanisms (infusate and aspiration) are operatively coupled to a single source of rotary power though each may operate independently (e.g., through the implementation of independent transmission mechanisms, (e.g., clutch packs, adjustable or fixed gearing, etc.).

In another embodiment, the aspiration pump only features a helical pump mechanism coupled to a source of rotary power. In this embodiment, the delivery of an infusate liquid may be accomplished by other methods, such as by high-pressure fluid delivery utilizing a reciprocating positive displacement pump in order to provide an adequate infusate liquid flow rate.

Figure 1:
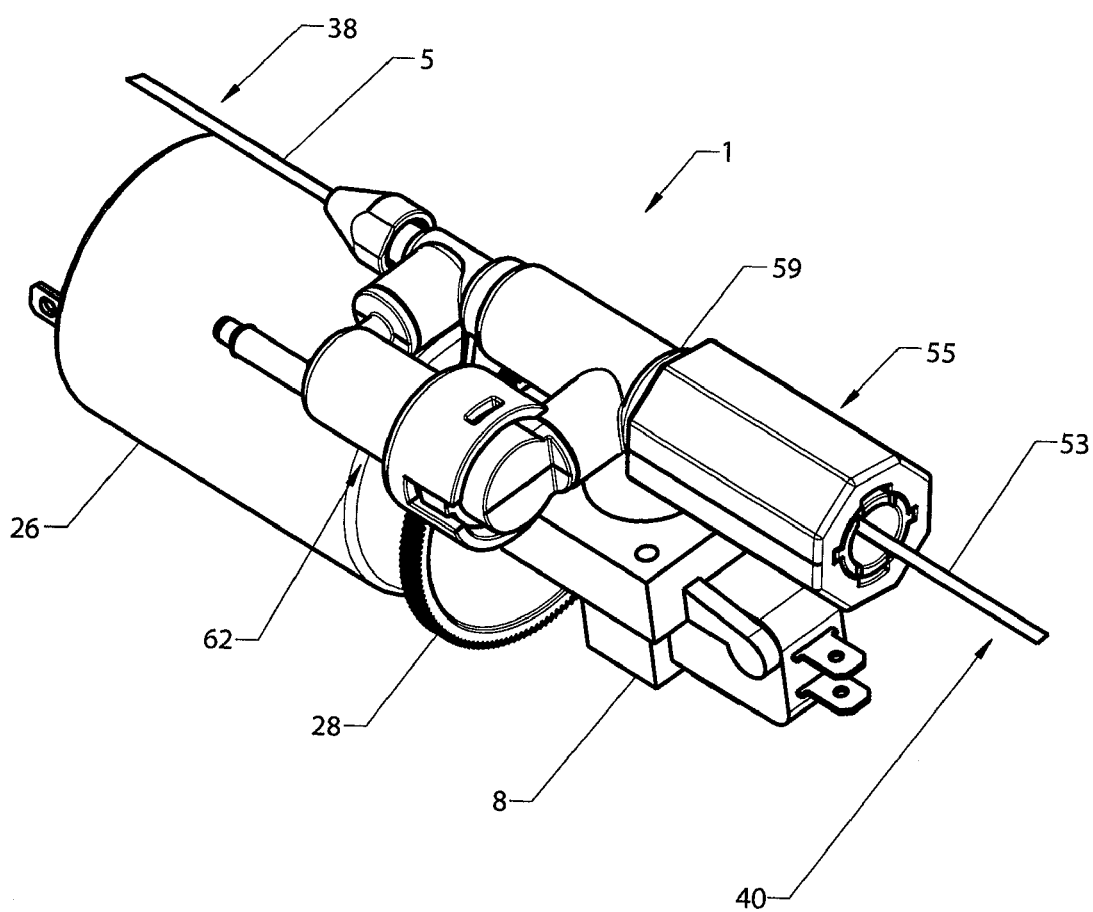
FIG. 1 depicts a perspective view of the catheter assembly.
Figure 2A:
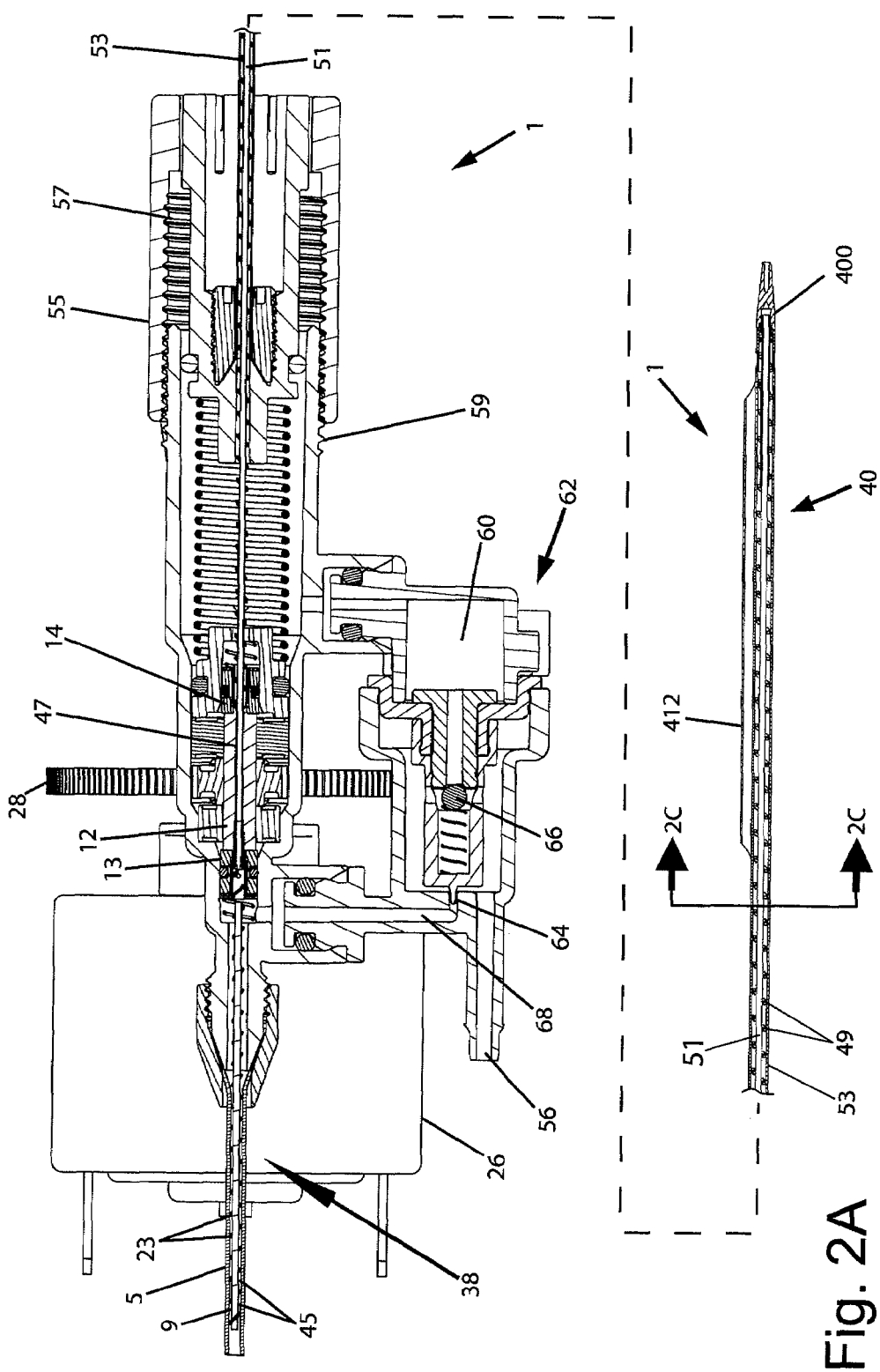
FIG. 2A depicts a cross-section view of the catheter assembly.

In one embodiment, as depicted in FIG. 1 and in exploded cross-section in FIG. 2A, the catheter assembly 1 is driven by a single motor 26 or other source of rotary power (e.g., electrical motor, air pressure turbine, hydraulic turbine, etc.), effectuating the rotation (i.e., via a gearing mechanism or transmission) of a hollow driveshaft 12. The drive shaft may be operatively coupled on its proximal side 12 to an infusate helical pump 38, and in fluid communication with an infusate liquid reservoir (not shown). The drive shaft 12 may also be operatively coupled on its distal end 14 to an aspiration helical pump 40, which may be directed into the patient and in fluid communication with the treatment area. The distal portion of the aspiration pump is shown in greater detail in FIG. 4, as will be discussed.

Figure 3:
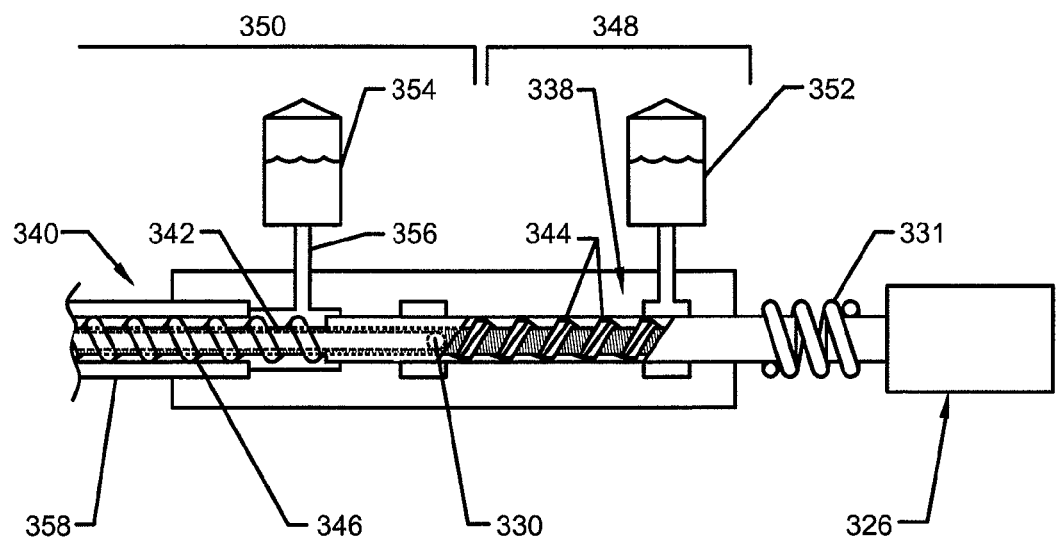
FIG. 3 depicts an alternate embodiment of the catheter assembly.

In another embodiment, as can be seen in FIG. 3, a motor 326 or other source of rotational power may serve to actuate the driveshaft 331, either directly (as shown) or indirectly through a transmission or gear mechanism (not shown), and the drive shaft may extend distally towards and into the body (not shown). In this embodiment, a single driveshaft 331 drives both the aspiration pump 340 and the infusate pump 338. The proximal portion 348 of the driveshaft 331 features a helical infusate pump 338, which has infusate windings 344 that when rotated by the driveshaft 331 creates infusate fluid flow distally towards the body from an infusate source 352. At the distal end of the infusate windings, the infusate liquid is directed through a port 330 into a hollow lumen of the core tube 342 forming the distal portion 350 of the driveshaft 331. The distal portion of the driveshaft features aspiration windings 346 for a helical aspiration pump 340.

In use, the infusate fluid is pressurized by the rotating positive displacement action of the infusate pump 338, and the infusate fluid is thereby directed through port 330 into the hollow lumen core tube 342 of the aspiration pump 340 and is delivered at the distal end of the assembly (as will be discussed later).

In a similar fashion as the infusate pump, the distal portion 350 of the driveshaft 331 features a hollow lumen core tube 342 around which is wound a coiled member to form aspiration windings 346 for a helical aspiration pump 340. As the single driveshaft 331 is rotated, the aspiration windings 346 forming a coiled member rotate within a catheter jacket 358, which causes the aspiration of debris proximally, which may then be directed towards a waste reservoir 354 by a waste lumen 356.

With reference to FIG. 2A, though applicable to any of the described embodiments, the assembly may incorporate a gear mechanism 28 or transmission operatively placed between the motor 26 and the drive shaft 12, wherein the gear mechanism serves to transfer a rotary power applied into rotation of the driveshaft 12 and the associated helical pump rotors (i.e., in a 1:1 ratio). Alternatively the gearing mechanism may serve to amplify the torque or turning power available for rotating the helical pump mechanisms (by a reduction in gearing of the motor relative to the helical pump rotors (e.g., 2:1 or 3:1, etc); most preferably, the gearing mechanism may serve to increase effective gearing in order to increase the rotational speed of the driveshaft (e.g., 1:2, 1:5, 1:50, etc.), so that a given number of turns by the motor will result in more turns of the helical pump rotors. A preferred embodiment features an increase in effective gearing to ensure that the small diameter helical pump rotors turning within the catheters are able to achieve adequate flow rates and pressures, as will be discussed.

The helical pump rotors generally, and as utilized for the infusate pump and aspiration pump of this assembly, are designed to turn within a surrounding jacket (e.g., a catheter or lumen), such that as the turning of the helical rotor occurs, a positive displacement pumping action is produced by the spirally wound helical pump rotor. This principle is based on an Archimedes pump or screw pump system. The screw pump system is capable of compact, powerful delivery of a substance. Furthermore, the screw pump is also effective at delivery of fluids and particulates, and is relatively unimpeded by the presence of solid materials or foreign debris. One benefit of the screw pump design is that the helical pumps are capable of transporting fluids or particulate materials having dimensions less than the spacing between the windings of the pump without clogging. A further benefit of the screw pump design is that the mechanical transmission of torque through the helical rotor may also serve to macerate or reduce the fragment size of the debris to more manageable levels, allowing material that would otherwise be too large to be transported.

Figure 2B:
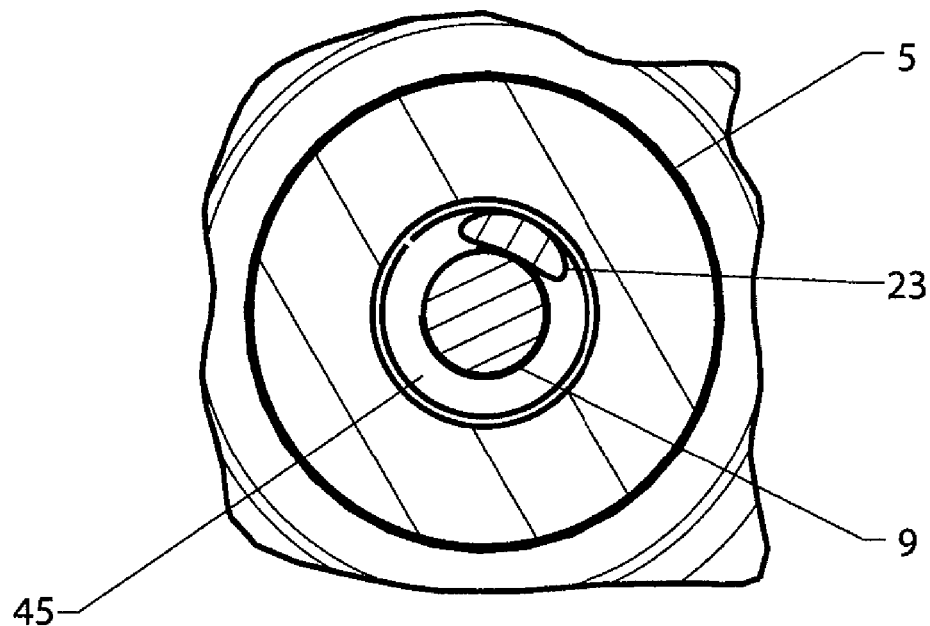
FIG. 2B depicts an end on, cross-section view of the infusate catheter assembly at the dashed line 2B of FIG. 2.

The effectiveness of a screw pump is dependent upon minimizing the amount of leakage that occurs between the helical pump rotor and the jacket. As will be appreciated by those skilled in the art, the rotation of a helical coil wire creates an Archimedes-like pumping action. For example, the infusate pump 38 of the present invention depicted in FIG. 2A and in cross-section in FIG. 2B creates a pumping action to aid in carrying an infusate liquid down an annular space or passageway 45, located between the infusate catheter jacket 5 and the infusate helical rotor, comprising a helical coiled member or wire 23 and an infusate core member 9.

Figure 2C:
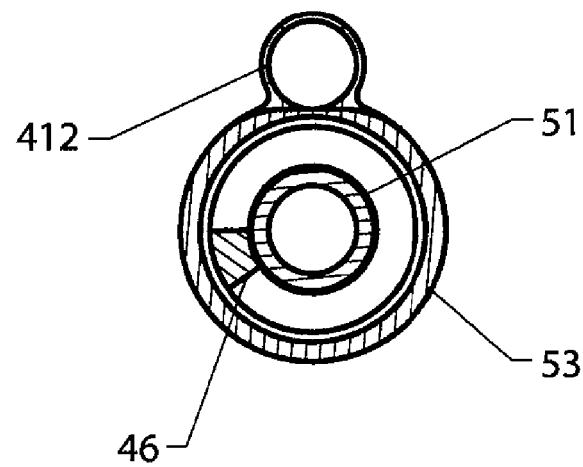
FIG. 2C depicts an end on, cross-section view of the aspiration catheter assembly at the dashed line 2C of FIG. 2.
Figure 4:
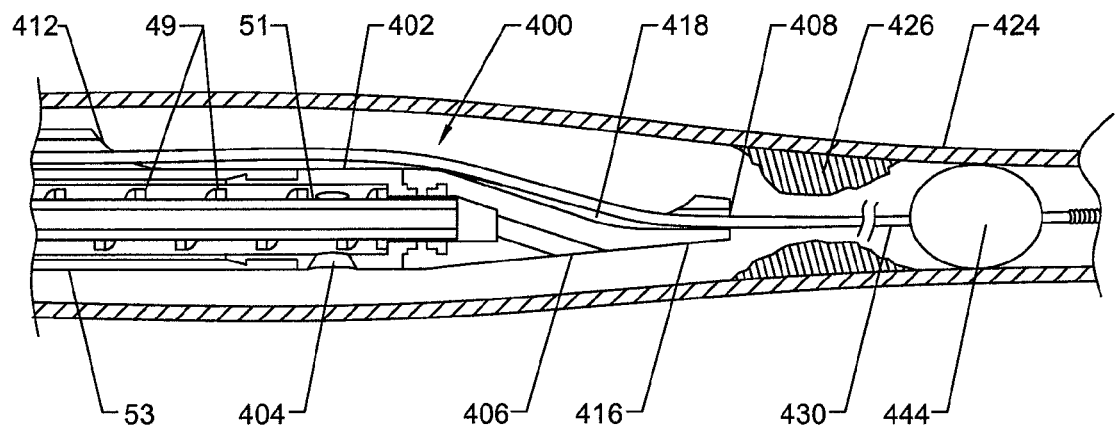
FIG. 4 depicts an enlarged cross-section view of the distal portion of the aspiration pump assembly placed in a vessel of a living being, and one embodiment of the distal end of the catheter assembly having a flexible atraumatic tip used in conjunction with a distal protection measure.

As a similar example, the aspiration pump 40 of the present invention is a helical pump mechanism as depicted in FIG. 2A, an expanded view in FIG. 4, and in cross-section in FIG. 2C. The aspiration pump 40 serves to create a pumping action to aid in carrying fluid and/or occlusive material proximally away from the treatment site, through the rotation of the windings of the aspiration coiled wire 49, which is arranged between the hollow aspiration core lumen 51 and the aspiration catheter jacket 53. Additionally, the hollow aspiration core lumen may allow the delivery of high pressure fluid to the distal end of the device. In this embodiment, the crossing profile of the inserted catheter remains small enough to reach into the more tortuous vasculature.

In particular, the ability of the helical coil wire 23 to deliver fluid flow is a function of: (a) the rotation speed of the helix, (b) the swept volume of the helix (the swept volume of the helix being the volume of fluid entrapped between the coils of one pitch of the helix), and (c) the leakage or backwards flow along the helix due to the clearance between the helical coiled wire 23 and the infusate catheter jacket 5, as well as the clearance between the helical coiled wire 23 and the infusate core 9. If the clearances are reduced to zero (and consequently the leakage is reduced to zero) the pump can act as a very stiff positive displacement pump, that is, it can deliver flow at a large range of output pressures regardless of the inlet pressure. Minimizing leakage is necessary to ensure suitable performance as a fluid delivery catheter system.

For a flexible helical pump, there is preferably some clearance between the rotating impeller or rotor of the helical pump, and the surrounding jacket. This clearance is required to ensure flexibility of the helical pump, to ensure the free rotation of the rotor while the pump is distorted by a bending force. The clearance required to ensure adequate flexibility and function of the catheter may be as much as 33% of the rotor diameter, but is typically around 10% or less. That is, the clearance between the rotor and the surrounding jacket will naturally vary as a bend is introduced, creating an ovalized cross-section in the outer jacket. The gap created through the distortion results in a greater tendency for backward leakage; furthermore, rotor turning resistance is increased due to greater friction through the narrowed dimension of the ovalized cross-section, and the rotor will resist the flexing force applied, creating more frictional losses. In order to compensate for the increased clearance as a consequence of the gap created by the flexed assembly, it is beneficial to increase the rotational speed of the helical rotor, to minimize backwards leakage. Other factors that influence the amount of backwards leakage in the helical pump system include the viscosity of the liquid being pumped, as high viscosity (thicker) fluids will not be able to leak through the gap as easily as a low viscosity (thinner) fluid; also the size and number of windings of the pump rotor are factors affecting backwards leakage, as specific amount of leakage past each turn will have less effect by virtue of the leakage being a smaller proportion of the total fluid pumped than in a design having a smaller rotor, less windings, or less length. For windings with a larger pitch (i.e., more space between each winding), the flow rate tends to be higher for a given rotational speed than a narrow pitch (i.e., less space between each winding.)

For the present invention, high rotational speeds are beneficial in ensuring acceptable performance as a catheter designed to be used within the vascular system of a living being. For a catheter to be used in the living being, sizes of around 3 French (F) to 8 F may be appropriate, and vary dependent upon intended usage, for example, 4-5 F for coronary vessels, 4-5 F for carotids, 5-8 F for femoral arteries, and 3-4 F for cerebral vessels, larger sizes may be required for larger vessels such as organ and esophageal use.

If an alternative use allows a greater pump diameter or less flexibility and consequently less clearance is acceptable for the alternative use (e.g., for use in an organ lumen, esophageal use, large diameter vessels, etc.), a device according to the present invention featuring reduced rotational velocity may be effective in achieving adequate pump flow rates. The helical coil pumps of the present invention may also feature variable windings or pitches of the coiled wires, in order to enhance flexibility or minimize vibrations, or achieve desired pumping characteristics.

In one embodiment, as depicted in FIG. 2A, there is attached to and extending proximally away from the driveshaft's proximal end 13 a helical infusate pump 38 having a helical rotor arranged to turn within the infusate catheter jacket 5. This rotor has an infusate core member 9 having a helical coil member or wire 23 wound around at least a portion or portions of the length of the core. The infusate catheter jacket 5 and rotor extend proximally away from the driveshaft 12, and operatively coupled to a source of fluid (not shown) for infusate delivery. As the drive shaft 12 is rotated by motor 26, the driveshaft in turn causes the rotation of the rotor of the infusate pump 38. The operation of the infusate pump 38 causes the infusate liquid to be drawn into the jacket 5 by the rotation of core 9 and helical coil wire 23. As the rotation continues, the infusate liquid is conveyed distally further into the infusate annular passageway 45, defined by the windings of the infusate helical coil wire 23, between the surrounding infusate catheter jacket and the infusate core 9.

As the helical infusate pump 38 is a positive displacement pump in one embodiment, the windings may not continue for the entire length of the infusate rotor, rather, the coiled windings may stop or be intermittent and rely on the pressure created by the windings to continue driving the fluid along in the lumen within the jacket. This embodiment may offer increased flexibility in the regions where there are no windings. Alternatively, the windings may continue for the length of the infusate pump 38, uninterrupted. In an embodiment, the pressurized infusate fluid flow is directed into a central lumen 47 in a hollow driveshaft 12, and further down a lumen within a core lumen 51 for the aspiration pump 40, to the distal end of the assembly, where it is delivered into the body (as will be discussed later).

Like the infusate helical pump embodiments discussed, the aspiration pump may also be a helical design, having a rotor comprising an aspiration core member or lumen 51 and a coiled member or wire 49 that rotate to transport fluids proximally. The coiled member is operatively coupled to the driveshaft 12, and rotates in unison with the driveshaft 12. In one embodiment, the aspiration pump rotor may feature an aspiration coiled member 49 in the form of wire wound into a coil about, and affixed to, the aspiration core lumen 51. In another embodiment of the aspiration rotor, there is an aspiration core lumen 51, segments of which feature a helical coiled member 49 wrapped around the core lumen 51. In this manner, adequate flow can be achieved, however flexibility is enhanced, as the regions without the coiled member would be able to conform to sharper bends without affecting flowrates significantly for the entire pumping mechanism. In an embodiment, the coiled member 51 is wound about a hollow central core lumen 51, but is not affixed thereon or affixed only at the proximal end of the coiled member 49, at or near the driveshaft 12. In this embodiment, the torque of the driveshaft 12 is transferred along the length of the aspiration coiled member 49 to the working head 400 at the distal end of the assembly (an enlarged view of which is shown in FIG. 4, to be discussed later). Furthermore, the coiled member 49 is spirally wound in an orientation such that as it is rotated, the coil would seek to expand in diameter, tending to unwind, and effectively enhancing the seal of the coiled member 49 against the outer aspiration catheter jacket 53. As the expanded coil member 49 is rotated, some wear occurs at the periphery of the coil wire, maintaining a cutting edge (as will be discussed later).

The Fluid Pathway

The fluid pathway, begins with a source of infusate fluid (e.g., a reservoir, bottle or supply etc.), preferably located near the patient, most preferably located at a level above the patient, in order to prevent free fluid flow backwards into the reservoir, yet not so high that substantial forward free flow occurs without pump activation. The infusate pump 38 draws in and pressurizes an infusate fluid.

It is recognized that the infusate may be a liquid (e.g., saline solution, buffer solution, water, etc.) delivered by the present invention in order to flush out debris. A contrast medium may be also be delivered as infusate in order to aid in guiding the catheter to the treatment site and direct the application of the present invention at the treatment site. Delivery of infusate may further include at least one biologically active agent or therapy (e.g., blood, or other oxygen carrying liquid, drugs/beneficial agents, etc.), a non-exhaustive list of examples of biologically active agents that may be delivered are enumerated in Table 1.

TABLE 1

Examples of Biological Active Ingredients

Adenovirus with or without genetic material
Alcohol
Amino Acids
    L-Arginine
Angiogenic agents
Angiotensin Converting Enzyme Inhibitors (ACE inhibitors)
Angiotensin II antagonists
Anti-angiogenic agents
Antiarrhythmics
Anti-bacterial agents
Antibiotics
    Erythromycin
    Penicillin
Anti-coagulants
    Heparin
Anti-growth factors
Anti-inflammatory agents
    Dexamethasone
    Aspirin
    Hydrocortisone
Antioxidants
Anti-platelet agents
    Forskolin
    GP IIb-IIIa inhibitors
    eptifibatide
Anti-proliferation agents
    Rho Kinase Inhibitors
    (+)-trans-4-(1-aminoethyl)-1-(4-pyridylcarbamoyl)
    cyclohexane
Anti-rejection agents
    Rapamycin
Anti-restenosis agents
    Adenosine A2A receptor agonists
Antisense
Antispasm agents
    Lidocaine
    Nitroglycerin
    Nicarpidine
Anti-thrombogenic agents
    Argatroban
    Fondaparinux
    Hirudin
    GP IIb/IIIa inhibitors
Anti-viral drugs
Arteriogenesis agents
    acidic fibroblast growth factor (aFGF)
    angiogenin
    angiotropin
    basic fibroblast growth factor (bFGF)
    Bone morphogenic proteins (BMP)
    epidermal growth factor (EGF)
    fibrin
    granulocyte-macrophage colony stimulating factor (GM-CSF)
    hepatocyte growth factor (HGF)
    HIF-1
    insulin growth factor-1 (IGF-1)
    interleukin-8 (IL-8)
    MAC-1
    nicotinamide
    platelet-derived endothelial cell growth factor (PD-ECGF)
    platelet-derived growth factor (PDGF)
    transforming growth factors alpha & beta (TGF-.alpha., TGF-beta.)
    tumor necrosis factor alpha (TNF-.alpha.)
    vascular endothelial growth factor (VEGF)
    vascular permeability factor (VPF)
Bacteria
Beta blocker
Blood clotting factor
Bone morphogenic proteins (BMP)
Calcium channel blockers
Carcinogens
Cells
Cellular materials
    Adipose cells
    Blood cells
    Bone marrow
    Cells with altered receptors or binding sites TABLE 1-continued Examples of Biological Active Ingredients Endothelial Cells
Epithelial cells
Fibroblasts
Genetically altered cells
Glycoproteins
Growth factors
Lipids
Liposomes
Macrophages
Mesenchymal stem cells
Progenitor cells
Reticulocytes
Skeletal muscle cells
Smooth muscle cells
Stem cells
Vesicles
Chemotherapeutic agents
    Ceramide
    Taxol
    Cisplatin
Cholesterol reducers
Chondroitin
Collagen Inhibitors
Colony stimulating factors
Coumadin
Cytokines prostaglandins
Dentin
Etretinate
Genetic material
Glucosamine
Glycosaminoglycans
GP IIb/IIIa inhibitors
    L-703,081
Granulocyte-macrophage colony stimulating factor (GM-CSF)
Growth factor antagonists or inhibitors
Growth factors
    Bone morphogenic proteins (BMPs)
    Core binding factor A
    Endothelial Cell Growth Factor (ECGF)
    Epidermal growth factor (EGF)
    Fibroblast Growth Factors (FGF)
    Hepatocyte growth factor (HGF)
    Insulin-like Growth Factors (e.g. IGF-I)
    Nerve growth factor (NGF)
    Platelet Derived Growth Factor (PDGF)
    Recombinant NGF (rhNGF)
    Tissue necrosis factor (TNF)
    Transforming growth factors alpha (TGF-alpha)
    Transforming growth factors beta (TGF-beta)
    Vascular Endothelial Growth Factor (VEGF)
    Vascular permeability factor (UPF)
    Acidic fibroblast growth factor (aFGF)
    Basic fibroblast growth factor (bFGF)
    Epidermal growth factor (EGF)
    Hepatocyte growth factor (HGF)
    Insulin growth factor-1 (IGF-1)
    Platelet-derived endothelial cell growth factor (PD-ECGF)
    Tumor necrosis factor alpha (TNF-.alpha.)
Growth hormones
Heparin sulfate proteoglycan
HMC-CoA reductase inhibitors (statins)
Hormones
Erythropoietin
Immoxidal
Immunosuppressant agents
inflammatory mediator
Insulin
Interleukins
Interlukin-8 (IL-8)
Interlukins
Lipid lowering agents
Lipo-proteins
Low-molecular weight heparin
Lymphocites
Lysine
MAC-1
Methylation inhibitors TABLE 1-continued Examples of Biological Active Ingredients Morphogens
Nitric oxide (NO)
Nucleotides
Peptides
Polyphenol
PR39
Proteins
Prostaglandins
Proteoglycans
    Perlecan
Radioactive materials
    Iodine - 125
    Iodine - 131
    Iridium - 192
    Palladium - 103
Radio-pharmaceuticals
Secondary Messengers
    Ceramide
Somatomedins
Statins
Stem Cells
Steroids
Thrombin
Thrombin inhibitor
Thrombolytics
Ticlid
Tyrosine kinase Inhibitors
    ST638
    AG-17
Vasodilators
    Histamine
    Forskolin
    Nitroglycerin
Vitamins
    E
    C
Yeast
Ziyphi fructus The infusate may also include solids or semisolids instead of fluid-only delivery. The solids may be suspended in solution. In any event, the solids must be of a particle size acceptable for use in helical pump systems, that is, of particle sizes capable of being delivered through a helical pump as provided. A non-exhaustive list of examples of solids or semi-solids that may be delivered are enumerated in Table 2.

TABLE 2

Examples of solids or semi-solids capable of being delivered by the present invention Alginate
Bioglass
Calcium
Calcium Phosphates
Ceramics
Chitin
Chitosan
Cyanoacrylate
Collagen
Dacron
Demineralized bone
Elastin
Fibrin
Gelatin
Glass
Gold
Hyaluronic acid
Hydrogels
Hydroxy apatite
Hydroxyethyl methacrylate
Hyaluronic Acid
Liposomes TABLE 2-continued Examples of solids or semi-solids capable of being
delivered by the present invention Mesenchymal cells
Nitinol
Osteoblasts
Oxidized regenerated cellulose
Phosphate glasses
Polyethylene glycol
Polyester
Polysaccharides
Polyvinyl alcohol
Platelets, blood cells
Radiopacifiers
Salts
Silicone
Silk
Steel (e.g. Stainless Steel)
Synthetic polymers
Thrombin
Titanium The inclusion of groups and subgroups in the tables is exemplary and for convenience only. The grouping does not indicate a preferred use or limitation on use of any material therein. For example, in Table 1, the groupings are for reference only and not meant to be limiting in any way (e.g., it is recognized that the Taxol formulations are used for chemotherapeutic applications as well as for anti-restenotic coatings). Additionally, the table is not exhaustive, as many other drugs and drug groups are contemplated for use in the current embodiments. There are naturally occurring and synthesized forms of many therapies, both existing and under development, and the table is meant to include both forms.

The infusate fluid becomes pressurized by the operation of the helical infusate pump 38 creating a positive displacement pumping action, coupled with the fluid resistance and drag of the infusate fluid in traveling a relatively small bore of both the infusate annular passageway 45 and the hollow lumen within the aspiration core lumen 51. Upon being expelled from the coils 23 of the infusate helical pump 38, the infusate liquid may be propelled along, under pressure, through the continuous lumen 45 defined within the infusate catheter jacket 5 for the infusate helical pump 38. The infusate liquid is then directed through at least one port (not shown) into a central lumen 47 within the hollow driveshaft 12. The central lumen 47 of the hollow driveshaft is in fluid communication with the hollow core lumen 51 of the aspiration helical pump 40. The pressurized infusate liquid travels through the lumen defined by the hollow core lumen 51, running the length of the aspiration pump 40, and the infusate is delivered through at least one outlet port in the working head 400, at or near the distal end of the assembly 1.

The infusate liquid delivery through the outlet port in the working head 400 may be in the form of high velocity, directed jets, streams or sprays, as required for a particular treatment methodology. Alternatively, either by reducing the flow rate or by providing a large enough delivery port or ports, the infusate pressure can be reduced such that the infusate liquid is delivered as a gentle wash or lavage, without much velocity to a target area. In the higher velocity delivery arrangement, the jets or streams may be oriented distally further into the body, radially away from the device and towards the walls of the lumen or vessel, or alternatively, directed back towards at least one inlet port for the removal by the pumping action of the aspiration pump. It is recognized that the fluid delivery may forcibly affect the material in the vessel or lumen (e.g., relying on currents or turbulence to fragment or separate the occlusive material or tissue). Alternatively, the target tissue to be treated may be subjected to the therapy or agent in the infusate fluid, which may cause a desired effect upon the target tissue, such that treatment may be effectuated. The characteristics of the fluid streams as delivered are largely determined by the pressure at which the infusate is delivered, and the design of the working head at the distal end (to be discussed later).

In an embodiment wherein the infusate delivery creates debris released from the vessel wall, the debris may be temporarily held in suspension in the mixture of bodily fluids and infusate fluid that has been delivered. In this embodiment, appropriate measures and care must be taken to contain or prevent the release of the generated debris into the body away from the site. This may be accomplished through the use of distal protection devices (e.g., umbrella filters, balloons etc.) as is known in the art.

In an embodiment of the present invention, opportunities for unique treatment methodologies are available. For example, during operation of the catheter, an infusate fluid containing a biologically active agent, such as a drug (e.g. table 2), or a particulate or semi-solid material (e.g. table 3) that may serve a benefit upon exposure to the tissue in the region may be introduced as described previously through the infusate fluid. Additionally, the procedure may be performed such that as the catheter is withdrawn, a column of infusate fluid is left remaining in the treatment site. Through the employment of a distal protection measure which serves to halt the flow of blood in the vessel, the column of infusate fluid is allowed to remain within the vessel for increased effectiveness of the treatment (such as through the longer delivery period of a biologically active agent to the tissue). The infusate fluid that remains in the region may allow increased opportunity for beneficial effect of the material or biologically active agent delivered in the infusate. This effect is especially noticeable in a situation where distal protection is utilized, as there is reduced or no through flow to quickly dissipate or remove the beneficial material.

In an alternative embodiment, the operation of the infusate pump 38 and aspiration pump 40 create a current or flow pattern that draws in released or fragmented occlusive material to the aspiration ports, thereby preventing the debris from traveling through the body away from the treatment site. That is, as the debris is generated by a fluid jet dislodging the material, a current flow is created that directs the material towards the aspiration port at the working head, and subsequently removed by operation of the aspiration pump.

In order to remove the occlusive matter debris and particulate material from the body, an aspiration pump 40 is provided in the assembly. The aspiration pump is most preferably in the form of a helical pump, extending distally from the driveshaft 12 into the body, and is a positive displacement pump. In an embodiment, the rotation of the drive shaft 12 causes the helical coiled member 49 to turn, resulting in conveyance of debris via screw pump fluid transport. The fluid flow rate for the delivery of infusate fluid may be at the same or different rate as the aspiration fluid flow. Most preferably the rate of aspiration is greater than that of the infusate delivery, in order to ensure complete removal of any debris generated. Care must be taken to prevent excessive blood loss and or collapse of the lumen due to unbalanced fluid flow rates.

In the embodiment depicted in FIG. 2A, there is an adjustment device 55 in order to maintain the appropriate positional relationship between the distal end of the coiled member 49 and the working head 400. The working head, shown in greater detail in FIG. 4, has at least one aspiration inlet port 404 and is operatively coupled to the aspiration catheter jacket 53, in which the coiled member 49 and the core member 51, together comprising the aspiration pump rotor, are arranged to rotate. As can be seen in FIG. 2A, the adjustment mechanism 55 may include an inner threaded element 59 and outer threaded element 57. Rotating the outer threaded element 57 may result in distal movement relative to the inner threaded element 59 (i.e., unscrewing), the aspiration catheter jacket 53 is then driven distally, as the proximal end of the aspiration catheter jacket 53 is operatively coupled to the outer threaded element 57. Conversely, rotation in the opposite direction causes proximal movement of the aspiration catheter jacket 53, and reduces any gap between the distal end of the coiled member 49 and the end of the catheter jacket 53. The adjustment device allows control of friction between the rotating coiled member 49 inside the cap 402 of the working head 400 located at the distal end of the aspiration catheter jacket 53. Furthermore, the adjustment mechanism 55 allows the proper placement of the windings of the coiled member 49 within the working head. The ability to adjust the position of the working head 400 relative to the distal end of the coiled member 49 is necessary to compensate for the effects of wear, bending and expansion of the coiled member 49. If the coiled member is significantly driven up against the inside surface of the working head while rotation is applied through the driveshaft 12, friction between the tip of the coiled member 49 and the working head 400 will reduce the rotation rate of the coiled member, in addition to causing excess wear and generating heat. In an embodiment providing for the adjustment device, an adjustment can be made to the positioning of the helical wire 49 relative to the inlet openings of the distal end, and ensure proper operation of the assembly.

As the helically coiled member 49 of the aspiration pump 40 rotates, the debris and fluid drawn in through the inlet ports 404 of the working head is conveyed proximally by the positive displacement action of the aspiration pump 40. Upon reaching the proximal terminus of the aspiration coiled member 49, the aspirant is driven into an evacuation chamber 60 in fluid communication with the lumen of the aspiration pump. In one embodiment, the evacuation chamber 60 may be a waste collection vessel (e.g., a bag, bottle, receptacle, etc.), or alternatively, the evacuation chamber may be part of a safety mechanism (to be discussed later) coupled to at least one pressure valve, which may then deliver the fluid to waste when appropriate.

The design of the aspiration pump 40, having a rotating helical coil member 49 and core lumen 51 within a surrounding jacket 53 may also provide the benefit of separating the occlusive material into components (e.g., a fibrin component and a blood component). This may occur with one design of the assembly, where the rotation of the coiled member 49 entrains the thrombus material, causing a wrapping action of the fibrin making up the thrombus. Additionally platelet material is removed from the treatment site as well through the same aspiration forces, however the nature of the platelets does not result in the same winding result that occurs with fibrous material. The fibrin winding action may allow the device to effectively remove fibrin and other occlusive material that is entangled within the fibrin, further exposing additional occlusive material for removal by the device that would otherwise have been shielded. Additionally, the winding action of the fibrin facilitates the targeting of removal of the clot, and minimizing the impact of the device upon the vessel wall.

In one embodiment, the aspiration pump 40 and infusate delivery methodologies 38 may operate independently (e.g., operate at different times, velocities, and rates). In this embodiment, appropriate precautions must be taken to prevent excessive delivery of infusate that may cause damage to the vessel or organ (e.g., rupture, hernia, etc.) Alternatively, precautions must be taken to prevent excess aspiration by drawing excessive fluid out from the body such that a localized reduced pressure environment is created, potentially causing a vessel collapse. Excess aspiration may potentially harm the patient by resulting excessive blood loss, and steps should be taken to avoid this occurrence. In the embodiment with independent aspiration and infusion, it may be useful to activate the aspiration pump 40 for a brief period of time prior to the activation of the infusate delivery. In this manner, any debris generated, whether through introduction of the device, by infusate delivery, or other mechanical means, will not be forced away from the target site, and instead will be directed out from the body through the assembly 1.

In the embodiment having a single motor 26 or source of rotary power, the aspiration pump 40 may be activated concurrently with the operation of the infusate delivery pump 38. In the most preferred embodiment, the flow rates of the infusate delivery pump 38 will be less than the flow rate of the aspiration pump 40 (e.g., 3:1 ratio of aspiration: infusion rates). In another embodiment, it is also recognized that the rate of infusate delivery can be equal to the rate of aspiration in order to minimize blood loss. In any of the embodiments, the safety of the patient may require steps to prevent debris release, such as through the use of distal protection devices (e.g., balloons, umbrella filters, etc.) This serves to ensure that the complete removal of the debris occurs, and prevents the debris from traveling through the body or blood stream with potentially harmful or fatal results.

The Safety Mechanism

In an embodiment of the invention, the aspiration 40 and infusate 38 pumps are driven off a single driveshaft 12, the driveshaft being propelled by a force applied to the driveshaft (e.g., electric motor, air turbine, hydraulic, etc.). With this embodiment among others, incorporation of a safety mechanism 62 may be beneficial. In operation, the activation of the driveshaft 12 may rotate both infusate 38 and aspiration pumps 40 concurrently, however infusate delivery through the distal end of the assembly preferably is not initiated until a safety mechanism 62 is actuated, as will be discussed.

In an embodiment of the invention, the safety mechanism 62 operates in response to a change in pressure in an evacuation chamber 60 in fluid communication with the lumen of the aspiration pump jacket 53. As the aspiration pump 40 is activated, the positive displacement pumping action of the helical coiled member 49 draws in fluid and debris material from the treatment site, conveying the aspirant proximally, towards the proximal end of the aspiration pump, and eventually through to the evacuation chamber 60, resulting in a pressure increase therein.

Prior to activation of the aspiration pumping action, the evacuation chamber 60 is subject to the body's blood pressure, as it is communicated through the fluid canal between the body and evacuation chamber, as defined by the lumen of the aspiration pump jacket 53. At these pressure levels, the safety mechanism 62 is not actuated to enable delivery of infusate fluid. While the safety mechanism 62 is not actuated, and the infusate pump 38 is rotating, any infusate fluid flow is directed towards a reservoir, rather than into the body. In this embodiment, the infusate fluid pathway is controlled by the safety mechanism 62 incorporating at least one valve, and preferably a first 64 and second 66 valve; the first valve 64 operating in response to the pressure within the evacuation chamber 60. Either of the valves of the safety mechanism may be controlled electronically or mechanically, operating in response to an increase in pressure within the evacuation chamber 60.

The safety mechanism of an embodiment, as depicted in FIG. 2A, features dual valves (first valve 64, and second valve 66) actuated mechanically in response to an increase in fluid pressure present in the evacuation chamber 60. In this embodiment, while the safety mechanism is subjected to lower pressures in the evacuation chamber, the infusate pathway to the treatment site through the hollow lumen of the aspiration core lumen 51 remains available for fluid flow; however, the path having the least fluid resistance is through the infusate bypass lumen 68 towards a waste reservoir. In this mode, substantially all infusate fluid flow is through the first safety valve 64 opening, and is shunted towards the waste reservoir through waste lumen 56, rather than through the distal arm of the assembly comprising the aspiration catheter 53 into the body.

As the aspiration pump 40 is engaged and conveys fluid and debris proximally and into the evacuation chamber 60, the positive displacement pumping action results in a pressure increase within the chamber, creating elevated pressure levels above that of the patient's blood pressure. The first safety valve 64 is then actuated by the pressure within the chamber (e.g., electronically or mechanically), and upon actuation, the infusate bypass lumen 68 fluid pathway that facilitated infusate flow directly towards the waste lumen 56 is sealed off, consequently the infusate fluid is directed towards the distal end and towards the treatment site via the hollow lumen within the aspiration core lumen 51.

As the pressure continues to increase, a second safety valve 66 is actuated. This second safety valve is actuated when the pressure within the aspiration fluid pathway, most preferably within the evacuation chamber 60, is at least as high as is required to activate the first safety valve 64. The second safety valve 66 remains closed at the lower pressures (e.g., blood pressure) and prevents fluid flow from the evacuation chamber towards the waste reservoir. Additionally, the second safety valve prevents the reverse flow of infusate fluid from the infusate bypass lumen 68 and first safety valve 64 into the evacuation chamber 60, and potentially through to the body via the aspiration pump 40. The second safety valve, while closed serves to prevent fluid flow between the evacuation chamber and the waste lumen 56. Upon actuation of the second safety valve 66, fluid flow from the evacuation chamber 60 towards the waste lumen 56 is allowed, and continues until the pressure actuating the second safety valve 66 drops below the pressure level required to maintain the second safety valve in an open state. The second safety valve may also be mechanically or electronically actuated. Most preferably, the second safety valve is a mechanical valve (e.g., a ball and spring check-valve arrangement) wherein the pressure within the evacuation chamber 60 causes the valve to open and allow fluid flow.

The design of the safety mechanism 62 serves to prevent infusate delivery without a corresponding activity of the aspiration pump 50. As pressure created by the aspiration pump is required to enable the delivery of infusate to the treatment site, should the aspiration pump suffer a failure (e.g., due to breakage, clog, etc.) the infusate delivery is disabled as the aspiration pressure drops, and the infusate liquid is then shunted towards the waste reservoir, rather than towards the patient.

In one embodiment, a warning mechanism (not shown) for the operator may be incorporated, as most likely, the operator would otherwise be unable to determine if the aspiration pump 40 was not operating properly. This is due to the fact that the driveshaft 12 will continue to be driven by the source of power, actuating the pumping mechanism regardless of a clog or failure of the components. This warning mechanism could be accomplished through the incorporation of a cut-off switch to halt the operation of the device or more preferably a warning indicator (e.g., a light, sound, etc.) to alert the operator as to the condition of the safety mechanism, either relying on the actuation of the first safety valve, the second safety valve, or alternatively by an entirely independent pressure switch in the fluid pathway.

An alternate embodiment of the safety mechanism may be incorporated into the present invention, in which the device is disabled (e.g., power to motor removed) if there is an imbalance or deviation from the desired pressures in the infusate and aspiration pump mechanism. For example, a sensor, or monitor could be utilized to track and respond to deviations in operation of the aspiration pump (e.g., deviations in aspiration pressure, aspiration flow rate, etc.), thereupon triggering a responsive event, such as alerting the operator to a malfunction, and/or disabling the device, at least temporarily. In FIG. 1, there is depicted an embodiment featuring a safety switch 8, that upon a deviation from a desired aspiration pressure, disables the automatic operation of the infusate pump.

In another embodiment, the safety mechanism 62 serves to prevent harm to the patient, such as may be accomplished by limiting the rate of flow (infusate and/or aspiration) from either or both of the infusion or aspiration pumps, or limiting or disabling the power source providing for the rotation of the infusion and/or aspiration rotor(s) of the catheter assembly. In an embodiment where the device relies on fluid circulating through one or both of the aspiration or infusate delivery lumens to maintain optimal temperatures, the safety mechanism 62 may also serve to prevent operation of the device at rotational speeds which might cause harm to the catheter assembly, were the temperatures not controlled.

Figure 12A:
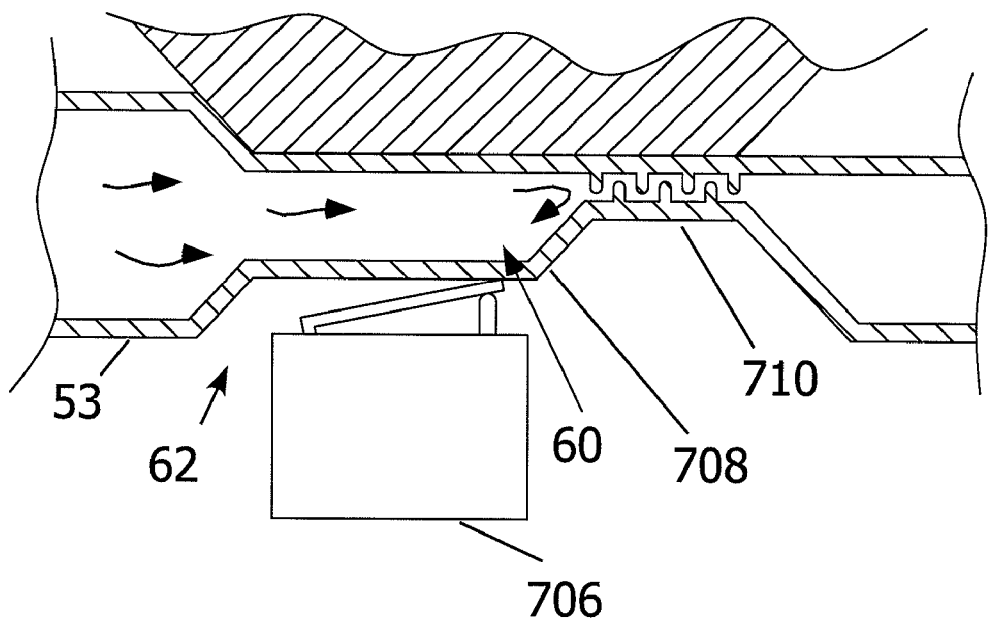
FIGS. 12A and 12B depict an embodiment of the safety mechanism of the catheter assembly in a low pressure or closed mode, and high pressure or open mode, respectively.
Figure 12B:
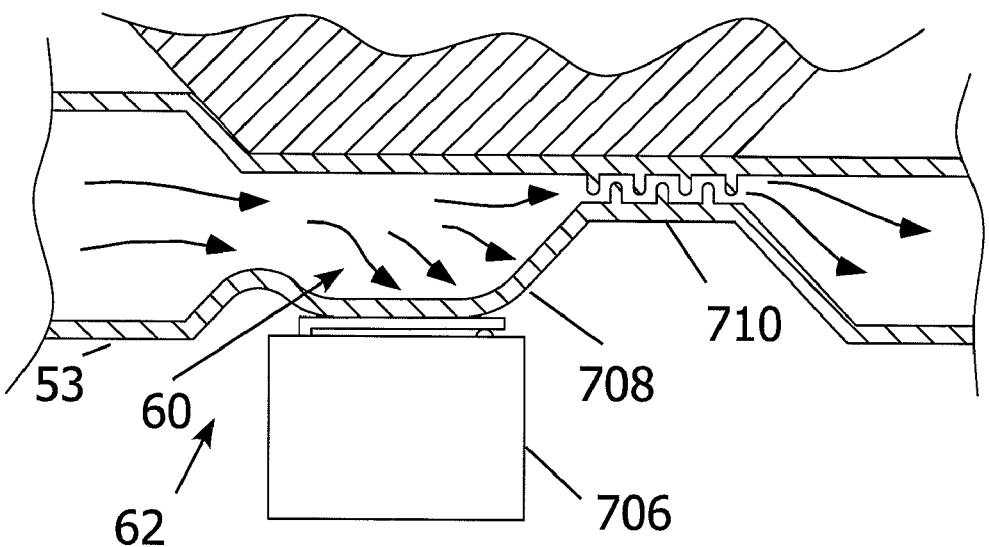

In an embodiment of a safety mechanism 62 depicted in FIGS. 12A and 12B, the safety mechanism is operated by a pressure generated by the operation of the catheter assembly. Preferably, the safety mechanism responds to a change in pressure within an evacuation chamber 60, which is in fluid communication with the lumen of the aspiration pump jacket 53. As depicted here, FIGS. 12A and 12B depict the evacuation chamber 60 as being directly connected to the aspiration catheter jacket 53, however, it is recognized that the evacuation chamber may be connected by a separate and distinct intervening lumen branching into the aspiration catheter jacket, or other methods of delivering pressure to the evacuation chamber as known in the art.

As depicted in FIG. 12A, the safety mechanism is shown in a closed or low pressure mode. In this mode, the pressure within the evacuation chamber 60 is not sufficient to cause the triggering of sensor or switch 706. For example, in an embodiment, a diaphragm 708 material may be caused to elastically expand in response to increasing pressure within the evacuation chamber 60. As the pressure within the evacuation chamber increases, the diaphragm translates this fluid pressure increase into motion, and as the diaphragm 708 distorts, it may activate a sensor or switch 706, as can be seen in FIG. 12B.

The pressure increase within the evacuation chamber may be facilitated by a restriction at the outlet of the evacuation chamber, such as a restriction, baffle, regulator or a pressure sensitive valve. For example, while in the low pressure mode of FIG. 12A, the fluid pressure within the evacuation chamber 60 is not high enough to cause the rapid escape of fluid through the baffle 710. The baffle 710 is constructed as a hollow lumen having internal projections which serve to slow the flow of low pressure fluid through the length of the baffle. As the pressure upon the fluid is increased, the fluid flow through the baffle 710 may increase in velocity, thereby allowing increased quantities of fluid to escape from the evacuation chamber 60. It is recognized that a narrowed lumen or constricted opening provide similar operation as the baffle shown. In any event, the safety mechanism features a flow restriction component to ensure that adequate pressure is preserved within the evacuation chamber 60 to maintain the elastic distortion of the diaphragm 708 as long as is necessary for proper operation of the device. It is recognized that the baffle need not completely block all fluid flow, as long as fluid flow rates, while above a minimum level, will result in the necessary pressure increase within the evacuation chamber 60.

As depicted in FIG. 12A, the baffle 710 will serve to slow fluid flow while there is low pressure within the evacuation chamber 60. As pressure increases, for example, in response to low speed operation of the device, the baffle 710 prevents a matching flow of fluid out of the evacuation chamber, until adequate pressure within the evacuation chamber is achieved; and as the pumping of the aspiration helical pump continues, the pressure within the evacuation chamber increases, causing diaphragm distortion. At or about the time the diaphragm triggers switch 706, the baffle will have less of an effect as at higher pressures, fluid velocity through the baffle will increase, allowing an amount of flow therethrough that matches the flow delivered by the pumping action, as is depicted in FIG. 12B.

Should there be a decrease in the pressure of the evacuation chamber (e.g., due to an obstruction in the fluid pathway leading to the evacuation chamber, or loss of pumping capability), the baffle 710 and diaphragm 708 will compensate by reverting back to the low pressure mode of FIG. 12A, preferably in proportion to the decrease in pressure experienced within the evacuation chamber 60. As the diaphragm 708 disengages from the sensor or switch 706, or alternatively triggers a second sensor (not shown), indicating a reduction in pressure within the chamber 60, the device responds by at least partially disabling the catheter assembly, such as by reducing or eliminating the source of power, thereby reducing pumping speeds or completely eliminating any pumping action altogether.

The Working Head

Figure 5:
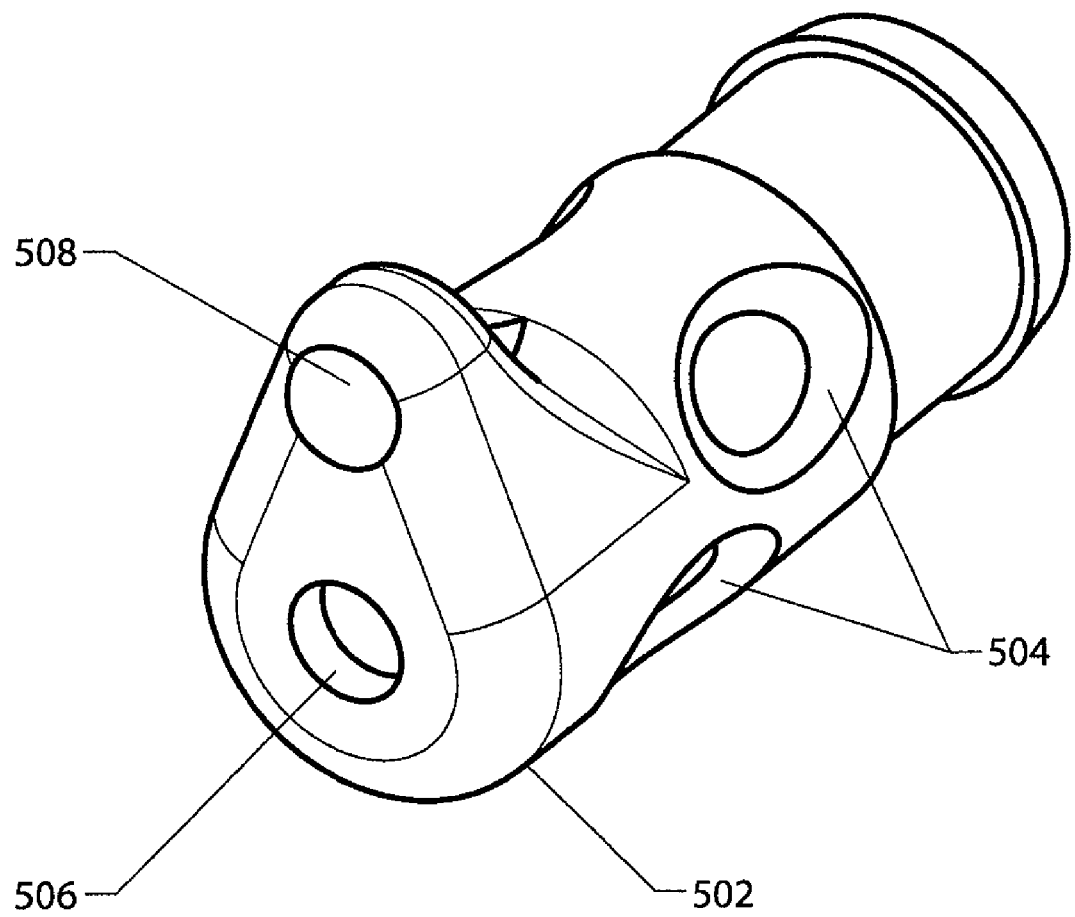
FIG. 5 depicts an enlarged view of an alternate embodiment of the distal end of the catheter assembly.
Figure 6:
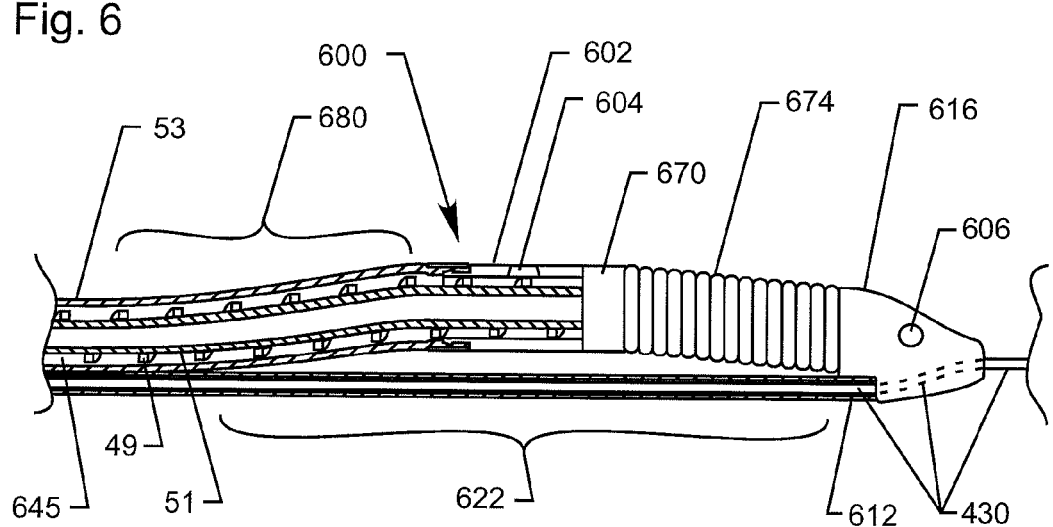
FIG. 6 depicts an enlarged partial cross-section view of a portion of the catheter assembly.

The assembly 1 features a working head 400 at the distal end of the assembly to be introduced into the patient for the procedure; examples of the working head are depicted in FIGS. 4, 5 and 6. As can be seen in FIG. 4, the working head 400 is operatively connected to the aspiration pump 40 of FIG. 2A. The working head features a cap 402 physically attached to the aspiration catheter jacket 53, and the helical coils of the aspiration coiled member 49 rotating within the cap. The working head in FIG. 4 is depicted placed in a vessel 424 of a living being, the assembly having been advanced as a monorail over a guidewire 430, in order to arrive at the treatment site, shown here having occlusive material 426, which may be a lesion, deposit or stenosis. At or near the distal end of the guidewire may be a distal protection measure 444, as shown. The distal protection measure serves to prevent debris from traveling away from the treatment site, such as by preventing the free flow of fluid with a balloon (as shown) or alternatively, such as through the use of a filter mechanism to capture any debris or loosened occlusive material 426. It is recognized that the use of the device may not require the use of distal protection, relying on the safe aspiration of fluid and occlusive material through the operation of the aspiration pump as described earlier.

Another embodiment of the cap portion of the working head is depicted by FIG. 5. As illustrated, the cap 502 provides at least one aspiration inlet port 504 to be located at or near the distal end of the assembly, thereby allowing material to pass through the inlet port 504, and, with reference to FIG. 2A, into contact with the aspiration coiled member 49 comprising the rotor of the aspiration pump 40 within the aspiration pump jacket catheter 53. The cap 502 also features an infusate delivery port 506, and a guidewire following means 508.

In a preferred embodiment, as depicted in FIG. 4, as the coiled member 49 of the aspiration pump rotates, the positive displacement action draws fluid and debris into the windings of the coiled member 49 through the aspiration inlet port 404. These inlet ports must be sized appropriately to ensure proper operation of the device. Inlet ports inappropriately sized by being too small in diameter will not allow occlusive material to enter into the aspiration jacket, similarly those that are too large will allow too much material to enter into the jacket and potentially clog the aspiration pump. Furthermore, adequate suction velocity must be maintained through the inlet ports. That is, the number and size of the inlet ports must be appropriate for the particular use, thereby not spreading the aspiration force over too large a surface area, which would otherwise result in too slow a velocity through the inlet ports to be effective in drawing in occlusive material. The number, size and shape of the inlet ports is determined empirically, and varies with the amount of suction created at the distal end by the rotation of the aspiration pump rotor, and the viscosity of the blood or material to be drawn in. Furthermore, the design of the rotating elements might determine the appropriate size and number of inlet ports (to be discussed later). Generally, a balance must be struck between too little suction velocity and too much material entering into the catheter jacket. An appropriate number and sizes of inlet ports will result in fragmentation of occlusive material into manageable sizes for the aspiration pump (i.e., less than the distance between adjacent windings of the coiled wire), and further provide for adequate flow rates generated by the rotation of the aspiration pump.

In one embodiment of the working head of the assembly, as depicted in FIG. 4, the inlet ports 404 have a sharp cutting edge forming the periphery of the port. In this embodiment, any material drawn into the windings of the aspiration rotor will be cut by the sharpened edge of the inlet ports, forming fragments of a size capable of being conveyed by the aspiration pump. The inlet ports may sit flush with the outer diameter of the jacket, or alternatively, and preferably, countersunk in order to prevent contact of a sharpened cutting edge with non-targeted tissue. The countersinking process may inherently produce a cutting edge, as can be seen in the depiction of a counter sunk inlet port 404 of FIG. 4.

In one embodiment, the aspiration coiled member 49 may also feature a cutting edge. In this embodiment, the coiled member may be at least partially formed having an acute edge that acts upon the target tissue. In a preferred embodiment, the aspiration coiled member at or near the distal end of the assembly has a cross-section comprising at least one edge (e.g., planar, triangular, rectangular, square, etc.) that serves to sever the tissue against the inlet port 404, cap 402, or aspiration catheter jacket 53, macerating the material into manageable sizes for the aspiration pump as the coiled member rotates.

In the alternative embodiment of an aspiration coiled member not having an edge (e.g., a round, pear shaped, oval cross-section etc.) the rotation of the coiled member may serve to sever the tissue against the aforementioned edge of an aspiration inlet port. In this or other embodiments, by rotatably conveying the aspirant material, the fibrin in the material may be further reduced into smaller fragments by the maceration as a consequence of the rotation of the cutting edge of the coiled member 49. The maceration occurs where thrombus material is further severed by the individual windings of the aspiration coiled member pinching the thrombus material against the inner surface of the cap 402 or the extraction catheter jacket 53.

In a preferred embodiment, depicted in FIG. 2, where the proximal end of the aspiration coiled member 49 is affixed only to the drive shaft 12 at the proximal end of the coiled member, as the torque is transmitted the length of the coiled member, there is a tendency for the coiled member to unwind, resulting in a larger outer diameter of the coiled member. The expansion of the coiled member is limited by the aspiration catheter jacket 53 entraining the aspiration pump mechanism 40. As the coiled member is rotated, and wear occurs between the coiled member 49 and the jacket 53, a cutting edge may be maintained upon the outside circumference of the coiled member, allowing it to more easily sever the tissue drawn in through the inlet port 404. Furthermore, the unwinding that occurs as the coiled member 49 is torqued also forces the coiled member outwards as it tends to unwind away from the central core lumen, and against at least one inlet port 404 at the distal end, further enhancing the ability of the assembly to fragment the occlusive material into more manageable fragment sizes.

FIG. 6 features an alternative embodiment of a working head 600, specifically the distal portion of the assembly designed for insertion into a patient for a procedure to remove occlusive material. Working head 600, of FIG. 6 may be operatively connected to the aspiration pump 40 of FIG. 2A as described previously, or to other aspiration mechanisms known in the art. The working head 600 consists of a can portion 602 physically attached to the aspiration catheter jacket 53, with the helical coils of the aspiration coiled member 49 rotating within the catheter jacket 53 and can 602. As illustrated, the can 602 provides at least one aspiration inlet port 604 to be located at or near the distal end of the assembly, thereby allowing material to pass through the inlet port 604, and into contact with the aspiration coiled member 49 within the aspiration pump jacket catheter 53. In one embodiment, the can portion 602 has an external diameter that is approximately the same as the adjacent catheter jacket 53. However, another embodiment may have an enlarged can portion, e.g. of greater diameter, (not shown) that would allow the device to more effectively treat occlusive materials in larger diameter vessels. The can may simply be a distal portion of the catheter jacket 53, or alternatively, the can may be an annular structure affixed to the distal end of the aspiration catheter jacket 53.

In practice, the working head is typically guided to the desired location within the body of a living being over guidewire 430, which may be loaded through the flexible atraumatic tip 616 and through the guidewire lumen 612. In another embodiment, guidewire lumen 612 can be a monorail guide, in which case the guidewire would travel for a short distance within lumen 612 until exiting a short distance more proximal from the end of the catheter (not shown). It is recognized that one or more radiopaque markers may be incorporated into the various locations on the device (e.g. can, retention bands, atraumatic tip, etc.) to allow visualization techniques to be utilized when placing the catheter.

Figure 7:
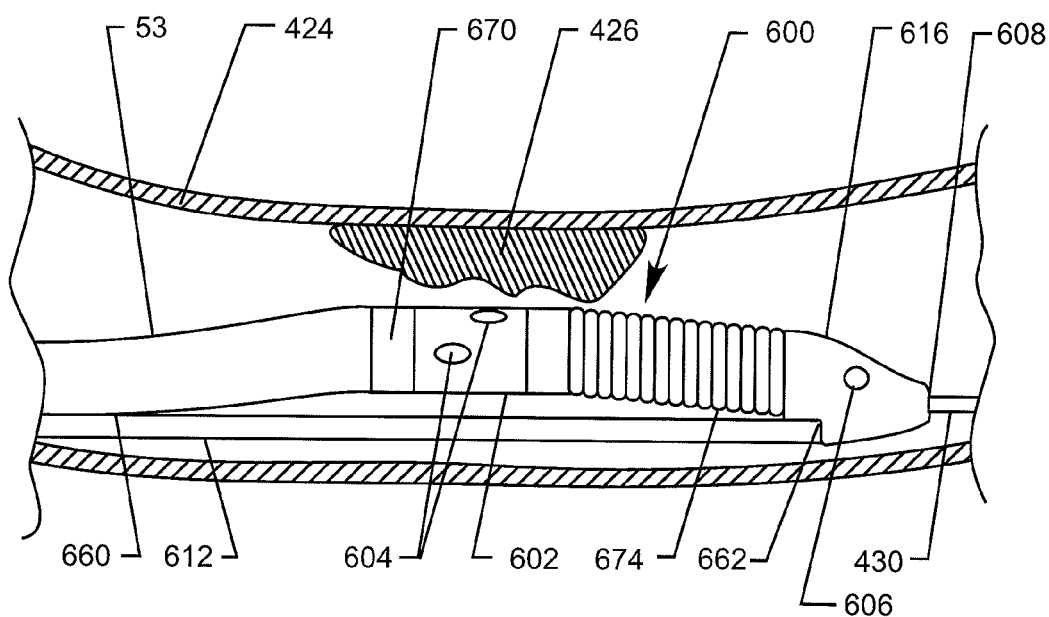
FIG. 7 depicts an enlarged view of the distal portion of one embodiment of the aspiration catheter placed in a vessel of a living being.

The working head 600 may also feature an angularly displaced portion 680 of the working head 600. In one embodiment, the angularly displaced portion 680 of the working head consists of an aspiration coiled wire 49 and hollow aspiration core wire 51 that, upon rotation causes the catheter jacket 53 to deflect away from (e.g., lateral, radial or orthogonal to) the guidewire lumen 612. There may be a benefit to providing an aspiration core wire 51 and coiled wire 49 that are pre-bent, imbalanced, or otherwise arranged to provide an enhanced movement of the working head 600 upon rotation of the core wire 51 and coiled wire 49. A pre-bent section may be laterally displaced by some amount, as shown in FIGS. 6 and 7, while at rest and absent the rotation of the aspiration pump components. Upon applying rotation to the aspiration pump components, the working head 600 will be caused to be laterally displaced from the guidewire a varying amount, as the rotation of the core wire 51 and coiled member 49 causes the working head to affect movement, in forms such as vibration, arc, orbit, scan, oscillation or precession. As stated earlier, pre-bending a portion of the device may enhance the direction, and extent of lateral displacement of the working head 600 away from the guidewire 430.

As has been described previously with reference to FIG. 1, the catheter assembly of FIG. 6 may similarly be driven by a single motor 26 or other source of rotary power (e.g., electrical motor, air pressure turbine, hydraulic turbine, etc.), effectuating the rotation (e.g., via a gearing mechanism or transmission) of a driveshaft 12. The driveshaft 12 may be hollow, and also may be operatively coupled on its distal end 14 to an aspiration helical pump 40, which in turn operates the helical coils 49 causing them to rotate within catheter jacket 53. As a result of rotation, and possibly combined with the angularly displaced portion 680 of the working head 600, the rotation of the aspiration helical pump will cause a portion of the working head to displace away from and then back towards the guidewire lumen 612. As a function of the rotational speed of the aspiration helical pump components, specifically, the core wire 51 and coiled wire 49, within the aspiration catheter jacket 53 and can 602, rotating at approximately 10,000 to approximately 150,000 RPM, preferably about 60,000 to about 110,000 RPM, the working head will seek to precess (i.e., via a precession path) away from the guidewire lumen and effectively scan the vessel as will be illustrated later. The rapid rotation of the aspiration pump may cause movement of the working head (e.g., vibrational, precessional, arcing, orbital movement) in a frequency range that is heavily dependent upon the materials of the device, as well as the local conditions, where the frequency of the movement of the head will correspond to, or be less than that of the rotational speed of the aspiration helical pump. It is also recognized that secondary or compound movement may occur during operation, for example, while the working head is moving as described previously, the working head may also be subject to additional movement patterns, albeit of smaller magnitude than the first movement. For example, it is recognized that the smaller magnitude movement may be an orbital movement occurring as the working head is traveling along a larger orbit, in a fashion similar to epicyclic movement. By controlling the displacement shape of the angularly displaced portion 680 of the working head, the movement of the working head can be optimized to best treat the occlusive material. It is recognized that the pre-bent section can take on a variety of shapes, such as being formed to mimic a sine wave, half of a sine wave, a square wave, a step function, a helix, corkscrew or any other 3-D pathway, or other desirable profiles.

In one embodiment, a flexible connector (e.g., flexible spring or resilient material) section 674 of the working head which is attached to at least the distal end of can 602 by means of retention band 670 or other fixation methods (e.g., adhesives, welding, soldering, etc.) provides the flexibility for the can portion 602 of the working head 600 to deflect away from the guidewire 430 and guidewire lumen 612. This flexible section can be constructed of a variety of resilient or flexible materials known in the art (e.g. steel, nitinol, plastic, etc.). It is also considered that the flexible spring section could be coated or covered with another material, such as polymer shrink wrap, to provide a fluid tight seal, and/or prevent the coil springs from trapping tissue or debris. Alternatively, the flexible section 674 may be incorporated into the flexible atraumatic tip 616, such as by lengthening the tip 616, where the tip is of a suitably flexible material and design, and where the tip is attached directly to retention band 670 thereby serving the function of a flexible spring.

Figure 11:
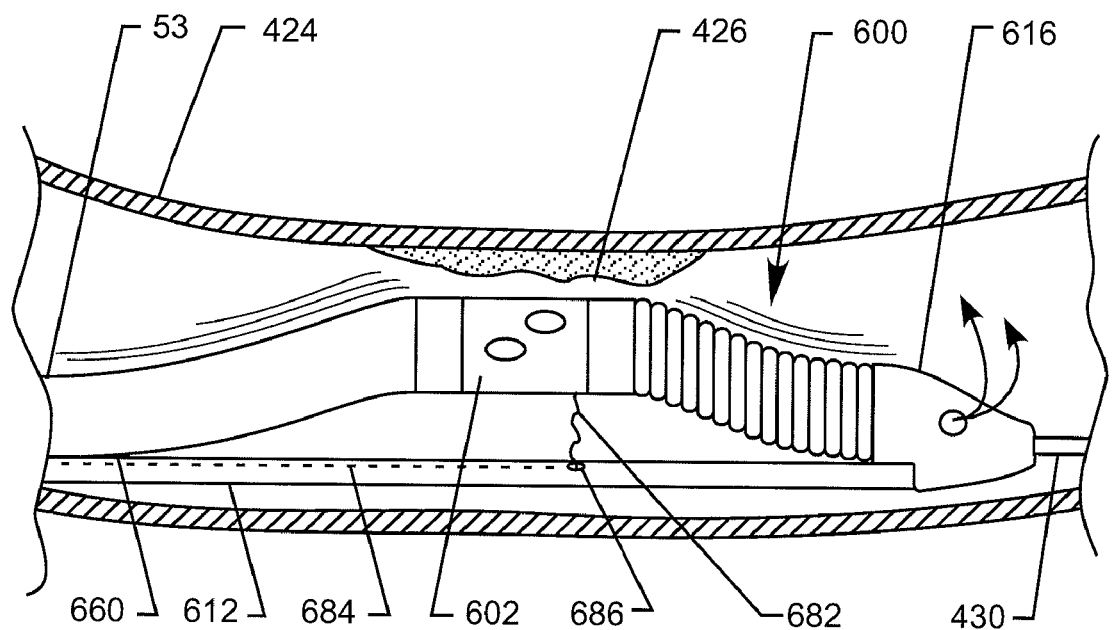
FIG. 11 depicts an alternate embodiment of the catheter assembly having a means for adjusting the degree of active separation between the guidewire and working head.

Varying the construction of the apparatus will allow one to tailor the extent to which the working head 600 can be laterally displaced away from the guidewire 430 or guidewire lumen 612. For example, the flexible connector material's length and construction may control the extent to which the flexible connector is able to deform in allowing lateral displacement or movement of the working head 600, relative to the guidewire 430, or guidewire lumen 612. Also, the amount of lateral displacement of the working head 600 may also affected by the length of un-attachment 622 as determined by the distance between the points at which the working head 600 is connected to the guidewire 430 or guidewire lumen 612. This un-attached region is depicted with more clarity in FIG. 7, where attachment points 660 and 662 define the un-attached region of the catheter. Additionally, the degree of angular deflection of section 680, along with the flexibility of catheter jacket 53 may combine to determine how far the can 602 is capable of deflecting from the guidewire lumen. These factors are not exhaustive of the methods by which the lateral displacement may be controlled, for example, it is recognized that a tether as shown in FIG. 11, may be incorporated into the device to limit the extent of displacement (to be discussed later). In another embodiment, there may be a single attachment point, where a guidewire following means is employed to guide the catheter along the guidewire, and the rest of the catheter is free to move independently from the guidewire. It is recognized that at least one tether may be utilized along with this embodiment as well.

As the coiled member 49 of the aspiration pump rotates, the positive displacement action draws fluid and debris into the windings of the coiled member 49 through the aspiration inlet port 604. As previously described, these inlet ports can be sized to optimize and ensure proper operation of the device. As also described previously, the shape and sharpness of the inlet port 604 can be designed to cooperate with an internal cutting element (e.g. aspiration coiled wire 49, cutting rotor, helical blades, shaver, or other cutting elements known in the art) to best cut and fragment the occlusive material while at the same time minimizing any unintended trauma to the healthy tissue of the living being. In general, the device provides a safe and reliable means of breaking down occlusive material (e.g. plaque, thrombus, etc.) with an exposed rotating cutting element. The rotating cutting element may consist of the helical system shown in this embodiment or may additionally utilize rotating blades, rotors, impellers or other means known in the art treating occlusive materials (e.g., U.S. Pat. Nos. 4,696,667; 5,261,877; 5,074,841; 5,284,486; and 5,873,882).

It is recognized that the various embodiments described herein may incorporate distal protection, for example as shown in FIG. 4, the distal end of the guidewire may incorporate a distal protection measure (e.g., balloon, filter, etc.) to prevent debris from traveling away from the treatment site.

FIG. 7 features an embodiment of distal end of the assembly working head 600 depicted as placed in a vessel 424 of a living being, the assembly having been advanced as a monorail over a guidewire 430, in order to arrive at the treatment site, shown here having occlusive material 426, which may be a lesion, deposit or stenosis. As is shown, the can portion 602 of the working head 600 is deflected slightly away from guidewire lumen 612. The guidewire lumen attaches to the catheter jacket 53 at attachment location 660 and the guidewire lumen 612 attaches to the distal portion of the working head at location 662. During operation the can portion 602 of the working head is caused to deflect away from the guide wire as a result of the rotation of the helically wound wire 49, and optionally, a pre-bent shape of the rotating components, which may cause the working head to affect movement, such as precess or orbit, and thereby move the working head 600 into a new location 602B (FIG. 8) within the vessel to better treat the occlusive material (in a manner similar to a jump rope). The movement of the working head may be limited as the catheter components (e.g., jacket, flexible connection and working head, encounter the guidewire or guidewire lumen. It is recognized that the path followed by the working head may not be a normal precession pathway or orbit, as during the movement, the catheter will have to traverse one side of the guidewire, rather than orbit entirely around the guidewire. This orbit or precess pathway may be biased directionally within the vessel, duct, lumen or other hollow organ structure. For this reason, there may be a benefit to the providing, in addition to the previously described movement of the working head 600, rotation along the axis of the catheter (e.g., manually or automatically rotating the catheter jacket), to allow the catheter to sweep a larger area, or perimeter of the vessel to remove debris.

Figure 8:
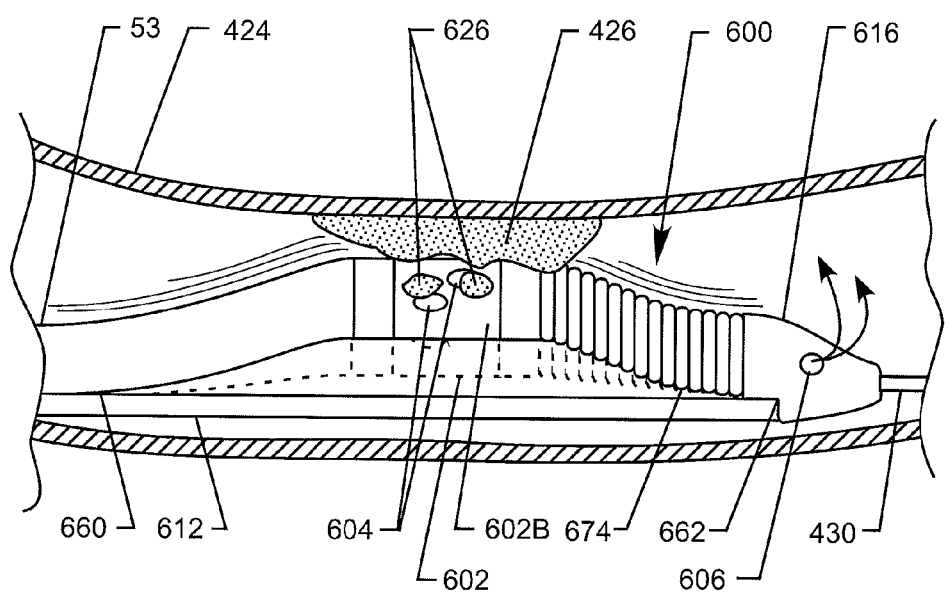
FIG. 8 depicts an enlarged view of the distal portion of one embodiment of the aspiration catheter operating to remove debris from the vessel of a living being.

FIG. 8 depicts the working head assembly 600 operating within vessel 424 of a living being. As described previously the source of rotary power effects rotation of the aspiration coiled wire 49 within the jacket 53 thereby causing a portion of the working head to undergo movement, as it is displaced away from and then back towards the guidewire lumen 612. As depicted in FIG. 8, this permits the catheter to expand the region where the working head 600 is able to contact and treat occlusive material. Infusate can be delivered into the vessel through the infusate delivery port 606 as described in previous embodiments. Aspiration of pieces of occlusive material 626 can occur through aspiration inlet ports 604. As illustrated, a catheter having a flexible portion and a working head, which can extend away from the guide wire such that the working head portion of the catheter can come within a closer proximity of the obstructive material allows a small diameter wire guided catheter to safely remove obstructions in a vessel or lumen which are located at a distance from the path of the guidewire.

Figure 9:
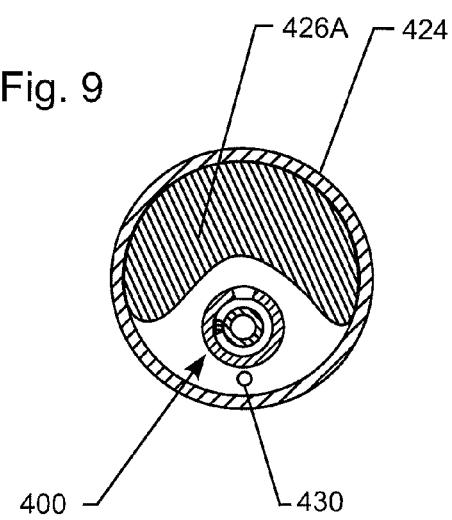
FIG. 9 depicts an end on, cross-section view of the aspiration catheter assembly within the vessel of the living being.
Figure 10:
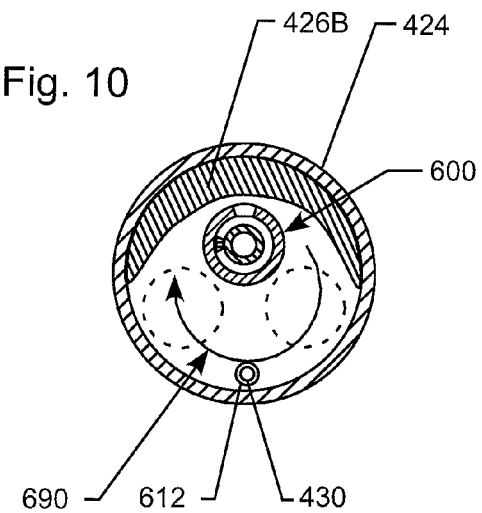
FIG. 10 depicts an end on, cross-section view of the aspiration catheter assembly operating to remove debris from within the vessel of the living being.

FIG. 9 depicts an end on, cross-section view of the aspiration catheter assembly 400 of FIG. 2A, within the vessel of the living being 424 as it is guided by guidewire 430. The working head 400 does not provide for the flexible spring portion, or extended unattached portion. FIG. 10 depicts an end on, cross-section view of the aspiration catheter assembly 600 operating to remove debris from within the vessel of the living being 424. The rotation of the aspiration coiled wire 49 within the jacket 53 thereby causing a portion of the working head 600 to translocate and be displaced away from and then back towards the guidewire 430 and guidewire lumen 612. The precessional action of the working head 600 causes it to travel along a path (e.g. such as shown by the path of working head in FIG. 10 represented by diagrammatically by arrow 690 and phantom lines) permitting the relatively small diameter device to contact and remove a greater amount of occlusive material from a larger diameter vessel, thereby reducing the amount of occlusive material 426B that remains within the vessel after the procedure. The device has the ability to precess, scan or oscillate within the vessel to treat a greater cross-sectional area at each location along the length of the vessel. It is anticipated that in some situations, the physical movement of the oscillating working head may help to disrupt or fragment the occlusive material. However, the catheter is designed such that by providing the working head with the ability to move closer to the occlusive debris, the vacuum created at the inlet ports 604, coupled with the cutting mechanism within can 602 will allow the device to have greater efficacy within larger vessels. Furthermore, the additives described previously may optionally be employed with this embodiment (e.g. drugs, such as thrombolytics).

FIG. 11 depicts an embodiment of working head 600 with at least one deflection limiting element (e.g., tether) 682 for controlling the effective area of activity scanned by the movement of the working head 600. Other technique for limiting the translational movement of the working head away from the guidewire 430 or guidewire lumen 612 may be applied, such as releasably arranged interlocking features, or adjustable slip rings that may be maneuvered to free up the working head for varying amounts of translational movement. As described previously, the length of un-attachment in combination with the degree of angular deflection, the flexibility of flexible connector section and the overall flexibility of the catheter jacket 53 in the region of the working head 600 all may determine how far the can 602 can deflect away from the guidewire lumen. A deflection-limiting tether 682 can be added to limit the distance that the can element 602 can travel away from the guidewire 430. This could allow the physician, surgeon, or other device operator to selectively expand the area of activity of the working head to gradually ease the device into large volumes of occlusive material. Despite the intended design of the catheter to not harm healthy tissue, this deflection-limiting tether 682 could serve to prevent the active area of the working head from contacting portions of the vessel wall. It could also be useful in treating vessels that change in diameter over their length. The tether could be adjusted to a short length in the small diameter portions and lengthened in the larger diameter vessel portions as necessary.

The deflection-limiting tether 682 consists of a filament that is connected fixably to a portion of the can portion 602 of working head 600. The filament extends from the can portion 602 into a hole 686 in lumen 612 and through a pathway 684 in the guidewire lumen back towards the proximal portion of the device where a control mechanism (not shown) such as a reel or cam can be used to tighten or release the tension on the tether. It is possible that the guidewire 430 and the tether 682 could share the same lumen along at least a portion of the device. It is also anticipated that in an alternate configuration the tether could be fixably attached to the guidewire lumen at location 686, extend to the can 602, into a pathway in can 602 (not shown) and then back through the catheter jacket via a pathway (not shown) to the proximal end of the device. A similar mechanism, known in the art could be used to tension and release tension in the tether. The pathway for the tether allows the tether to move freely. Ribbons, wires, retractable sleeves, and other mechanisms which can actively control the working head of the catheter with respect to the guidewire or guidewire lumen can also be used to limit the deflection of the working head.

It must be pointed out that the lateral displacement of the various embodiments of the present invention is not limited solely to thrombectomy catheters, and particularly rotational thrombectomy catheters. In particular, there may be a benefit to a device capable of having the working head displaced laterally as has been described, where the device incorporates an instrument having any other type of working head, e.g., fluid jets, atherectomy, rotary cutting, rotary abrasive, balloon angioplasty, a catheter for injecting a restriction-removing or dissolving liquid, an ultrasonic catheter, a laser catheter, a stent-delivery catheter, etc., for opening a lumen in an occluded vessel. Thus, a system constructed in accordance with any embodiment of this invention may make use of any instrument having any type of working head to open the lumen in the occlusive material in the blood vessel. Examples of other devices incorporating working heads are the Amplatz Thrombectomy Device designated by the trademark CLOT BUSTER by Microvena Corporation, the ANGIOJET device by Possis, the SILVERHAWK device by Foxhollow, the TURBO laser catheter by Spectranetics, the ORBITAL Atherectomy catheter by Cardiovascular System and the PATHWAY by Pathway Medical. It should also be pointed out that the working head of the device need not even engage the occlusive material, so long as its lumen-opening operation. In short, any type of instrument for opening a lumen through the occlusive material can benefit from use in the system of this invention, i.e., a system which allows a small diameter wire-guided catheter to act upon and treat occlusive material which is located at a distance from the guidewire. To that end the term "working head" as used herein is meant to include any type of device for operating on an occluded vessel to open a lumen in that vessel to the freer flow of blood therethrough.

In another embodiment of the device having a working head capable of being laterally displaced away from the guidewire, it is recognized that by increasing the diameter of the guidewire following means 508, or the guidewire lumen 612, at least in the region of the working head, it may be possible to provide for movement of the working head, at least to the extent that the guidewire following lumens are able to be displaced relative to the guidewire.

Guidewire Arrangement

The present invention may be operated either with or without a standard guidewire in place. If no guidewire is to be in place during operation of the instrument, a standard guidewire may be utilized for the purposes of aiding the navigation of the device to the treatment site (e.g., through tortuous vasculature) using techniques known in the art. Once in place, the guidewire may be removed, in order to allow operation of the present invention. Alternatively, the device may be placed in position without the assistance of a standard guidewire, using catheterization techniques known in the art.

In an embodiment where the assembly is to be operated with a guidewire in place, the device may follow along a guidewire running through a central coaxial lumen within the device (not shown). In a preferred embodiment, the device navigates following a guidewire in a monorail fashion. In the monorail embodiment, the assembly travels alongside the guidewire, and at least a portion of the catheter is operatively coupled to the guidewire. The delivery of the assembly to the target site is accomplished by the assembly traveling alongside the pre-placed guidewire to arrive at the target destination. This monorail embodiment provides a further benefit for it allows a central bore of the aspiration core lumen to remain unobstructed for delivery of infusate. In this embodiment, at or near the distal end of the device there is provided an opening for the guidewire to pass through, and ensures that device follows along the guidewire to arrive at the treatment site.

In the embodiment of the working head of the assembly depicted in FIG. 4, the device is arranged to slidably follow the guidewire in monorail fashion, additionally there may be provided an additional exterior guidewire lumen 412 to ensure the device more closely tracks the path of the guidewire, in order to prevent harm to the vasculature of the patient. This may be accomplished by providing an exterior lumen side-by-side with the aspiration pump, for maintaining close proximity to the guidewire, the guidewire lumen having a distal end located proximately of the working head of the device. In this embodiment, the cross-section of the device at the working end is minimized and flexibility is enhanced, further allowing the device to travel more tortuous bends without causing damage to the patient, as at least a portion of the guidewire near the distal end of the assembly is free to flex independently of the aspiration catheter jacket.

In the preferred embodiment of the working head of the assembly depicted in FIGS. 6-8, the device is arranged to slidably follow the guidewire in monorail fashion, and in these embodiments there is an exterior guidewire lumen 612 that bridges the gap from the flexible atraumatic tip 616 to a more proximal portion of the catheter jacket 53 at location 660. This exterior guidewire lumen helps to prevent the tip of the catheter assembly from prolapsing, a condition that could occur if tip 616 ceased advancing on guidewire 430 (e.g. jammed) while continued advancement forces on the catheter jacket could cause location 660 and 662 to approach one another and cause the working head section of the catheter to buckle. In an alternate embodiment (not shown) the bridging guidewire lumen 612 can be shortened, modified or even removed from section 662 of the working head 600, much like the embodiment of FIG. 4. To prevent catheter prolapse in this situation the distal portion of the catheter could be strengthened with higher durometer polymers or materials such as Nitinol to provide a durable yet flexible design that is resistant to buckling.

In order to assist in preparing the device for insertion into a body, there may be a benefit to providing a removable tool that would assist the user in the loading of the catheter onto the guidewire. For example, in the instance where backloading of the guidewire into guidewire following means or guidewire lumen of the catheter proves necessary, a loading tool may be provided to ensure that the guidewire is directed appropriately into the guidewire following means and guidewire lumen. The removable tool may provide, for example, a funnel to place the guidewire, and restrict the independent movement of the guidewire away from the catheter until the guidewire is securely loaded into the guidewire lumen or other guidewire following means, at which point, the loading tool may be removed to allow advancing the catheter into the body over the guidewire.

With reference to FIG. 5, there is depicted one embodiment of the working head 500, featuring a cap 502 having at least one aspiration inlet port 504, an infusate delivery port 506, and a guidewire following means 508. The guidewire following means features an opening in the distal tip, through which a guidewire may be slidably arranged. In this manner, the catheter assembly can follow along the guidewire as the assembly is urged further into the body, in order to arrive at the treatment site.

In a preferred embodiment, as depicted in FIG. 4, there is provided a flexible atraumatic tip 416 at the distal end of the working head 400, the atraumatic tip being operatively attached to the cap 402 of the working head. The atraumatic tip 416 is preferably a compliant biocompatible material (e.g., nitinol, silicone, latex, PTFE, etc.), or a compliant material coated with a biocompatible coating to enhance slidability, and features an opening 408 at the distal end of the atraumatic tip through which a guidewire may be slidably arranged. In use, the compliant atraumatic tip 416 is able to conform to the bend of the vessel, in order to help guide the catheter as it is urged further into the patient. The flexible atraumatic tip 416 may further feature a recessed area or channel 418 in order to accommodate a portion of the guidewire, further reducing the cross-sectional area of the atraumatic tip as it follows the guidewire. The design of this embodiment enhances the ability of the device to navigate bends in narrow vessels, without causing harm to the vessel, as the distal tip of the working head 400 with the flexible atraumatic tip 416 more easily navigates the bends and helps conform the vasculature to accept the passage of the assembly. This embodiment featuring a flexible atraumatic tip 416 may also feature the side-by-side guidewire lumen 412, as discussed above. As shown, the guidewire (not shown) would be free to flex independently of the device for a portion running alongside working head 400 of the device. The independently flexible portion of the guidewire would serve to ensure that the guidewire is not interfering with the bend of the catheter in traversing a sharp narrow bend in the vasculature, as the guidewire would be displaced alongside the bending of the catheter, rather than affixed on the outside or the inside of the bend, and further adding to the cross-section that needs to be bent in order to comply with the vasculature.

It is recognized the device may also feature distal protection measures (not shown). For example, in the embodiment of the device using a guidewire in a monorail fashion, the guidewire may have at least one distal protection measure (e.g., expandable balloon, umbrella filter, etc.) that serves to ensure debris or material is not released away from the treatment site during the course of the procedure. With the device following along the guidewire in a monorail fashion, there is no need for the guide wire, with or without a distal protection measure, to traverse through the interior of the length of the device, and adding to the crossing profile. The device featuring a distal end as depicted in FIG. 5 may be especially suitable for use with distal protection devices. The cap 502, having a relatively short length extending distally beyond the aspiration inlet ports 504, may serve to reduce the amount of occlusive material that may remain up against the distal protection device.

Thus since the invention disclosed herein may be embodied in other specific forms without departing from the spirit or general characteristics thereof, some of which forms have been indicated, the embodiments described herein are to be considered in all respects illustrative and not restrictive, by applying current or future knowledge. The scope of the invention is to be indicated by the appended claims, rather than by the foregoing description, and all changes which come within the meaning and range of equivalency of the claims are intended to be embraced therein.

What is claimed is:

1. A catheter system for introduction into a vessel of a living being to treat occlusive material, said system comprising:
   (a) a catheter having a proximal region, a distal region and a housing extending therebetween, said housing comprising an aspiration catheter jacket and defining a lumen, the housing further including a segment comprising at least one aspiration port near the distal region, the aspiration port being in fluid communication with the lumen,
   (b) a holding arrangement for holding a guidewire adjacent to the catheter at two spaced-apart points such that the segment is located between the two spaced-apart points, and wherein the segment may move in a laterally curved path towards said guidewire and away from said guidewire such that the catheter jacket within the segment becomes separated from the guidewire by a separation distance, and
   (c) an aspiration pump comprising a source of rotary power at said proximal region and a helical wire located in said lumen and extending from said distal region of said catheter to said proximal region and attached to said source of rotary power; wherein at least a portion of said catheter at the distal region is sufficiently flexible or deflectable as to allow the segment to deflect away from said guidewire such that the catheter jacket within the segment is separated from the guidewire by the separation distance when said source of rotary power is energized and rotates said helical wire in said lumen.

2. The catheter system of claim 1, further comprising an infusate pump.

3. The catheter system of claim 2, wherein said infusate pump comprises a rotary helical infusate pump.

4. The catheter system of claim 2, wherein said aspiration pump comprises a rotor within said aspiration catheter jacket, said rotor comprising a hollow core lumen and a helical wire, said hollow core lumen being arranged to allow delivery of an infusate fluid from said infusate pump to a vessel, duct or other hollow organ structure.

5. The catheter system of claim 4, wherein said aspiration pump further comprises a clearance between said rotor and said surrounding aspiration catheter jacket, said clearance being arranged to allow free rotation of said rotor within said surrounding aspiration catheter jacket while flexed, said free rotation being of sufficiently high speed to overcome leakage due to said clearance.

6. The catheter system of claim 4, further comprising at least one outlet port, said at least one outlet port being arranged to allow how of said infusate fluid therethrough to the vessel, duct and other hollow organ structure.

7. The catheter system of claim 6, wherein said at least one outlet port directs the flow of said infusate fluid in at least one direction selected from the group consisting of radially, distally, and proximally.

8. The catheter system of claim 3, wherein said rotary aspiration pump and said rotary helical infusate pump are both driven by said source of rotary power.

9. The catheter system of claim 3, wherein said aspiration pump and said rotary helical infusate pump are both driven at the same rotary speed.

10. The catheter system of claim 6, wherein said aspiration pump operates to create an aspiration flow rate, and said infusate pump operates to create an infusate flow rate, said aspiration flow rate being equal to or greater than that of the infusate flow rate.

11. The catheter system of claim 10, further comprising a safety mechanism comprising a fluid flow restrictor component and a pressure detection means comprising a diaphragm and pressure switch.

12. The catheter system of claim 11, wherein said pressure switch in a first state actuates the operation of a low pressure mode characterized by a lower rate of rotation of said rotor, and in a second state actuates the operation of a high pressure mode characterized by a higher rate of rotation than when said pressure switch is in a first state.

13. The catheter system of claim 6, further comprising a guidewire following means.

14. The catheter system of claim 13, further comprising a flexible atraumatic tip, a recessed channel, and a guidewire opening.

15. The catheter system of claim 14, wherein the flexible atraumatic tip comprises a biocompatible material selected from the group consisting of nitinol, silicone, latex, and polytetrafluoroethylene.

16. The catheter system of claim 14, wherein the flexible atraumatic tip further comprises a lubricious coating layer.

17. The catheter system of claim 1, further comprising means for fragmenting and aspirating said occlusive material to the distal portion of said flexible catheter.

18. The catheter system of claim 1, further comprising a driveshaft connected between said source of rotary power and said helical wire.

19. The catheter system of claim 1, further comprising a translational movement limiting means for limiting lateral movement of the aspiration catheter jacket relative to the guidewire.

20. The catheter system of claim 19, wherein said translational movement limiting means comprises at least one tether attached to said guidewire and to said catheter at said distal region.

21. The catheter system of claim 1, wherein said segment further comprises a can portion comprising said aspiration port.

22. The catheter system of claim 21, wherein said segment comprises an angularly displaced portion.

23. The catheter system of claim 1, wherein said helical wire is pre-bent, unbalanced, or otherwise arranged to provide an increase in the separation distance.

24. A system for clearing an accumulation of occlusive material from a vessel, duct or lumen in a living being, said system comprising:
  a flexible catheter comprising a proximal end, a distal end, and structure therebetween comprising an aspiration pump comprising a helical wire, a jacket for housing said helical wire, an inlet port at or near said distal end in fluid communication with said jacket, and an outlet port at or near said proximal end, and wherein the jacket includes a segment defining a plurality of aspiration ports near the distal end;
  a source of rotary power for rotating said helical wire,
  a holding arrangement that secures a guidewire to a distal end of said flexible catheter, wherein the holding arrangement holds the guidewire adjacent to the flexible catheter at two spaced-apart points on either side of the segment such that the segment may move laterally relative to the guidewire; and
  wherein the segment of said flexible catheter may move in a laterally curved path towards said guidewire and away from said guidewire when said source of rotary power is activated such that the segment of the flexible catheter is a farther distance from said guidewire when said source of rotary power is activated as compared to when said source of rotary power is not activated.

25. A catheter system for introduction into a vessel of a living being to treat occlusive material, said system comprising:
  a catheter having a proximal region, a distal region and a housing extending therebetween, the catheter further having a segment at the distal region that includes at least one aspiration port;
  a holding arrangement for holding a guidewire adjacent to the catheter at two spaced-apart points such that the segment of the distal region of the catheter that is positioned between the two spaced-apart points may move in a laterally curved path towards said guidewire and away from said guidewire such that the segment of the distal region of the catheter between the two spaced-apart points becomes separated from the guidewire by a separation distance, and
  an aspiration pump;
  wherein at least a portion of said catheter at the distal region is sufficiently flexible or deflectable as to allow the segment to deflect away from said guidewire by the separation distance when said aspiration pump is actuated.

* * * * *